US 12,233,119 B2

(12) United States Patent
Singh

(10) Patent No.: US 12,233,119 B2
(45) Date of Patent: Feb. 25, 2025

(54) COMPOSITION FOR ORAL OR NASAL DELIVERY OF TETANUS, DIPHTHERIA, AND PERTUSSIS VACCINE ALONE OR IN COMBINATION USING NEUROTOXIN ASSOCIATED PROTEINS

(71) Applicant: Prime Bio, Inc., North Dartmouth, MA (US)

(72) Inventor: Bal Ram Singh, Rehoboth, MA (US)

(73) Assignee: Prime Bio, Inc., North Dartmouth, MA (US)

( * ) Notice: Subject to any disclaimer, the term of this patent is extended or adjusted under 35 U.S.C. 154(b) by 0 days.

(21) Appl. No.: 18/467,682

(22) Filed: Sep. 14, 2023

(65) Prior Publication Data

US 2024/0131137 A1    Apr. 25, 2024
US 2024/0226262 A9    Jul. 11, 2024

Related U.S. Application Data

(62) Division of application No. 15/064,651, filed on Mar. 9, 2016, now Pat. No. 11,771,752.

(51) Int. Cl.
| | |
|---|---|
| *A61K 39/02* | (2006.01) |
| *A61K 39/00* | (2006.01) |
| *A61K 39/08* | (2006.01) |
| *A61K 39/395* | (2006.01) |
| *A61P 31/04* | (2006.01) |
| *C07K 14/19* | (2006.01) |
| *C07K 14/235* | (2006.01) |
| *C07K 14/33* | (2006.01) |
| *C07K 14/34* | (2006.01) |
| *C12N 15/62* | (2006.01) |
| *C12N 15/66* | (2006.01) |
| *C12N 15/70* | (2006.01) |

(52) U.S. Cl.
CPC ........ *A61K 39/099* (2013.01); *A61K 39/0018* (2013.01); *A61K 39/08* (2013.01); *A61K 39/39525* (2013.01); *A61P 31/04* (2018.01); *C07K 14/19* (2013.01); *C07K 14/235* (2013.01); *C07K 14/33* (2013.01); *C07K 14/34* (2013.01); *C12N 15/62* (2013.01); *C12N 15/66* (2013.01); *C12N 15/70* (2013.01); *A61K 2039/542* (2013.01); *A61K 2039/6031* (2013.01); *A61K 2039/622* (2013.01)

(58) Field of Classification Search
None
See application file for complete search history.

(56) References Cited

PUBLICATIONS

Lam et al (Curr Opin. Struct. Biol, 31:89-95, 2015).*

* cited by examiner

*Primary Examiner* — Brian Gangle

(57) ABSTRACT

The present invention describes a second-generation tetanus toxoid vaccine and a process for the preparation thereof, comprising the steps of: inducing an *E. coli* culture $OD_{600}=0.5$ by adding 0.2 mM IPTG; growing the culture at 14-16° C. for 14 to 20 hours; suspending the culture in 25 mM phosphate buffer containing 200 mM sodium chloride; adding 1% of triton-X-100 to the phosphate buffer, and adding the buffer to the culture; sonicating the culture for a period of 3 minutes (at 5 sec on/off pulse) at 4° C. on cold beads; centrifuging the culture for 60 to 90 minutes; collecting and purifying a supernatant using Ni-NTA affinity column with an eluant; and combining the supernatant into a pool with contaminated bands and concentrating using Centriprep-30 centrifuge filters (30 kDa pores).

6 Claims, 14 Drawing Sheets

Specification includes a Sequence Listing.

```
TXTATGTATCATATAACAATAATGAGCACATTGTAGGTTATCCGAAAGATGGAAATGCCT 3660
TTAATAATCTTGATACAATTCTAAGAGTAGGTTATAATGCCCCAGTATCCGTCTTTATA 3720
AAAAAATGGAAGCAGTAAAATTGCGTGATTTAAAAACCTATTCTGTACAACTTAAATTAT 3780
ATGATGATAAAAATGCATCTTTAGGACTAGTAGGTACCATAATGGTCAAATAGGCAACG 3840
ATCCAAATAGGGATATATTAATTGCAAGCAACTGGTACTTTAATCATTTAAAAGATAAAA 3900
TTTAGGATGTGATTGGTACTTTGTACCTACAGATGAAGGATGGACAAATGAT         3960
                                                                    6X His
         [TAA]GGCCTGCAGCCAAGCTTAATTAGCTGAGCTTGGACTCCTGTTGATA 4020
GATCCAGTAATGACCTGAGAACTCCATCTGGATTTGTTCAGAACGCTCGGTTGCCGCCGG 4080
GCGTTTTTTATTGGTGAGAATCCAAGCTAGCTTGGCGAGATTTTCAGGAGCTAAGGAAGC 4140
TAAATGGAGAAAAAATCACTGGATATACCACCGTTGATATATCCAATGGCATCGTAA 4200
AGAACATTTTGAGGCATTTCAGTCAGTTGCTCAATGTACCTATAACCAGACCGTTCAGCT 4260
GGATATTACGGCCTTTTTAAAGACCGTAAAGAAAAATAAGCACAAGTTTTATCCGGCCTT 4320
TATTCACATTCTTGCCCGCCTGATGAATGCTCATCCGGAATTTCGTATGGCAATGAAAGA 4380
CGGTGAGCTGGTGATATGGGATAGTGTTCACCCTTGTTACACCGTTTTCCATGAGCAAAC 4440
TGAAACGTTTTCATGGCTCTGGAGTGAATACCACGACGATTTCCGGCAGTTTCTACACAT 4500
ATATTCGC 4508
```

COMPOSITION FOR ORAL OR NASAL DELIVERY OF TETANUS, DIPHTHERIA, AND PERTUSSIS VACCINE ALONE OR IN COMBINATION USING NEUROTOXIN ASSOCIATED PROTEINS

CROSS-REFERENCE

This application is a divisional of U.S. patent application Ser. No. 15/065,651, filed on Mar. 9, 2016, now allowed, the entirety of which is incorporated herein by reference. The instant application contains a Sequence Listing which has been submitted electronically in ST.26 XML format. Said XML copy, created on Sep. 13, 2023, is named "Composition for Oral or nasal delivery of tetanus_3 sequence listing.xml" and is 16,000 bytes in size. The sequence listing is filed concurrently with the specification, thus is part of the specification and is incorporated by reference herein in its entirety.

TECHNICAL FIELD

This invention relates to a composition vaccine in combination with neurotoxin associated proteins for oral or nasal delivery of the vaccine. Moreover, the present invention particularly relates to oral delivery of tetanus vaccine with the help of proteins known as neurotoxin associated proteins (NAPs) from *Clostridium botulinum*. The NAPs combine with vaccine candidates made of domains of tetanus neurotoxin or detoxified recombinant tetanus neurotoxin (DrTeNT) for the delivery of the tetanus vaccines by oral or nasal passage.

BACKGROUND OF THE INVENTION

Botulinum neurotoxins (BoNT), one of the most toxic substance known to man, is produced by *Clostridium botulinum*. The clostridial neurotoxin family comprises seven BoNT serotypes (A-G), produced mainly by as a complex with a group of neurotoxin-associated proteins (NAPs). The botulinum neurotoxin complex is the only known example of a protein complex where a group of proteins (NAPs) protect another protein (BoNT) against acidity and proteases of the GI tract. The clostridial neurotoxin family comprises seven BoNT serotypes (A-G), produced mainly by *Clostridium botulinum* and the tetanus neurotoxin (TeNT), produced by *Clostridium tetani*. Although the BoNTs and TeNT function via a similar initial physiological mechanism of action, producing paralysis by inhibition of neurotransmission. BoNTs are synthesized as a single polypeptide chain comprising several domains with distinct functions that contribute to the mechanism of toxicity. Other proteins produced from *Clostridium botulinum* form a complex with BoNT that may contribute to toxicity and the stability of the BoNT in the natural environment of food poisoning. These proteins are known as Neurotoxin Associated Proteins (NAPs). When pure BoNT is exposed to the digestive conditions with acidic fluid and proteases, BoNT degrade into inactive small peptides. Thus, the pure BoNT exerts no oral toxicity. The toxicity exerts only when the BoNT is associated with NAPs, which protect BoNT against acidity and proteases of the GI tract. The NAPs not only protect BoNTs from the acidity and proteases of the GI tract but also assist in translocation of BoNT across the gut wall.

Tetanus is often a fatal disease caused by tetanus neurotoxin (TeNT) produced by *Clostridium tetani*, the same family of *Clostridium botulinum*, which can infect wounds resulting from general cuts, needle use, unhygienic birth practices. Tetanus is a disease that is entirely preventable with immunization of the population with tetanus toxoid vaccine. The tetanus toxoid vaccine is readily available at health clinics. The tetanus vaccination has become common throughout the world at least during infant ages. Later, booster shots are recommended for whole population every 10 years.

One hundred percent tetanus immunization is needed for the world population as this is a disease which often turns fatal. In addition, there is a need for booster shots of tetanus every 10 years, which frequently is overlooked. The current delivery system for tetanus vaccine involves needle injection, which is inconvenient and frightening for many people, especially to children. Currently there are over 200,000 annual tetanus deaths (mostly maternal and neonatal) worldwide which could be prevented with effective immunization. Therefore, tetanus vaccine is an ideal system for the development of an oral or intranasal delivery system.

There is a great need for child vaccination by developing a needle free immunization system for a much-needed tetanus vaccination. Currently, most vaccines are still injected into the body by needles. It is stressful and painful, especially to young children who get most of their vaccines at early ages. An oral delivery method proposed for administration of tetanus vaccine will be less painful, and safer. There will be no issue of contaminated needles.

Further, currently many vaccines cannot be delivered by an oral route because of the harsh digestive conditions in the stomach, like very low pH and bile acid, and proteases. Moreover, currently there are several safety concerns related to the injection of vaccines, e.g., allergic reaction, and contaminated antigen.

The TeNT has over 35% sequence homology with BoNTs, and shares much of the structural and functional features of BoNT, but is not a food poison due to the lack of NAPs. NAPs from one serotype of BoNT binding and protecting another serotype of BoNT, therefore NAPs can also bind, protect and translocate vaccines across the gut wall, specially TeNT or TeNT vaccine due to sequence homology. Therefore, the present invention uses NAPs of botulinum neurotoxin for oral and intranasal delivery of vaccines, specially tetanus vaccine.

At present tetanus vaccine is prepared by treating tetanus toxin with formaldehyde, trace amount of formaldehyde is left in the vaccine to prevent possible reversion. Formaldehyde causes adverse effect upon injection.

Further, currently tetanus vaccination is recommended every 10 years, most of the adult population is not up to date on tetanus vaccination due to the difficulties associated with administration of the vaccination.

Formalin-inactivated Tetanus toxoid is currently used for the immunization. It is recommended to give three to four doses in the childhood and booster dose to adult every 10 years. Tetanus toxoid is available in combination with Diphtheria and Pertussis. The present mode of administration of the Formalin-inactivated Tetanus toxoid is alone or in combination with Diphtheria and Pertussis as intramuscular injection. On the intramuscular injection local reactions consisting of pain, erythema, tenderness and induration at the injection site are common and may be associated with systemic reactions including transient fever and irritability. The reactions are basically due to the formalin present in the formulation. Thus, there is a continual need to develop oral tetanus vaccine alone or in combination with diphtheria and pertussis.

Availability of an oral delivery system would facilitate the vaccination schemes for pregnant women, infants and the world population in general. Currently no such vaccine delivery system is available, nor is there any effort known to be underway in this direction.

The present invention can solve the problem of harsh digestive conditions in the stomach like very low pH and bile acid, and proteases by using NAPs as adjuvants to protect the recombinant protein vaccines to go through this harsh condition. Further, with the present invention, NAPs protect the heavy chain of tetanus toxoid or recombinant detoxified tetanus neurotoxin from intestinal enzymes and facilitates the vaccine to evoke the immune response.

Further, the present invention solves the problem of safety concerns related to the injection of vaccines by not requiring an injection.

Further, the present invention solves the problem of introduction of formaldehyde. The present invention will eliminate the possibility of the introduction of formaldehyde to the patient both due to the novel method of preparation of the vaccine and delivery system.

Further, the present invention will solve the problems associated with the recommended administering of an injection, because the present invention is an oral/intranasal vaccination, and it will allow mass vaccination by untrained workers, or even self-vaccination.

Further, the present invention will solve the problem associated with the rapid release of the vaccine. Because the present invention is delivered as an oral or intranasal vaccine, it will have a slower release rate compared to injection.

Further, the present invention will solve the above-mentioned problems related to injections. The present invention is an oral vaccine, where NAPs as well as the mucous in the digestion system will provide possible protection against the above-mentioned safety issues.

Further, NAPs in the vaccine formulation will increase the bioavailability of the vaccine when administered orally or intranasally.

BRIEF DESCRIPTION OF THE DRAWINGS

FIG. 1 shows a diagram of botulinum neurotoxin and its associated proteins.

FIG. 2 shows a diagram illustrating pTeH plasmid, which is 8461 bp in length, comprising TeNT heavy chain, TeNT HC 2580 bp in length cloned in pET32a vector between BamHI and HindIII sites, fused with thioredoxin-tag (Trx-Tag) and His-tag at N-terminal.

FIG. 5A shows a first page of the nucleotide sequence of DrTeNT (3951 bp, including stop codon), which encodes for the full-length double mutant tetanus gene; and this sequence is submitted as Sequence ID No. 3 (SEQ ID NO: 3).

FIG. 5B shows a second page of the nucleotide sequence of FIG. 5A.

FIG. 5C shows a third page of the nucleotide sequence of FIG. 5A.

FIG. 6A shows a first page of amino acid sequence alignment of DrTeNT (SEQ ID NO: 1), reference (data from wildtype genomic DNA); and this sequence is submitted as SEQ ID NO: 2 and CN3911 from GenBank.

FIG. 6B shows a second page of the amino acid sequence of FIG. 6A.

FIG. 8A shows Dr TeNT was purified by using NTA column. Dr TeNT has his-tag at C-terminal and the molecular weight of Dr TeNT is about 150 kDa, and the protein eluted from column around 100 mm-200 mM Imidazole.

FIG. 8B shows the purified Dr TeNT.

FIG. 12. The immune response of the proposed construct with oral delivery as well as subcutaneous delivery.

OBJECT OF THE INVENTION

Figure 3:
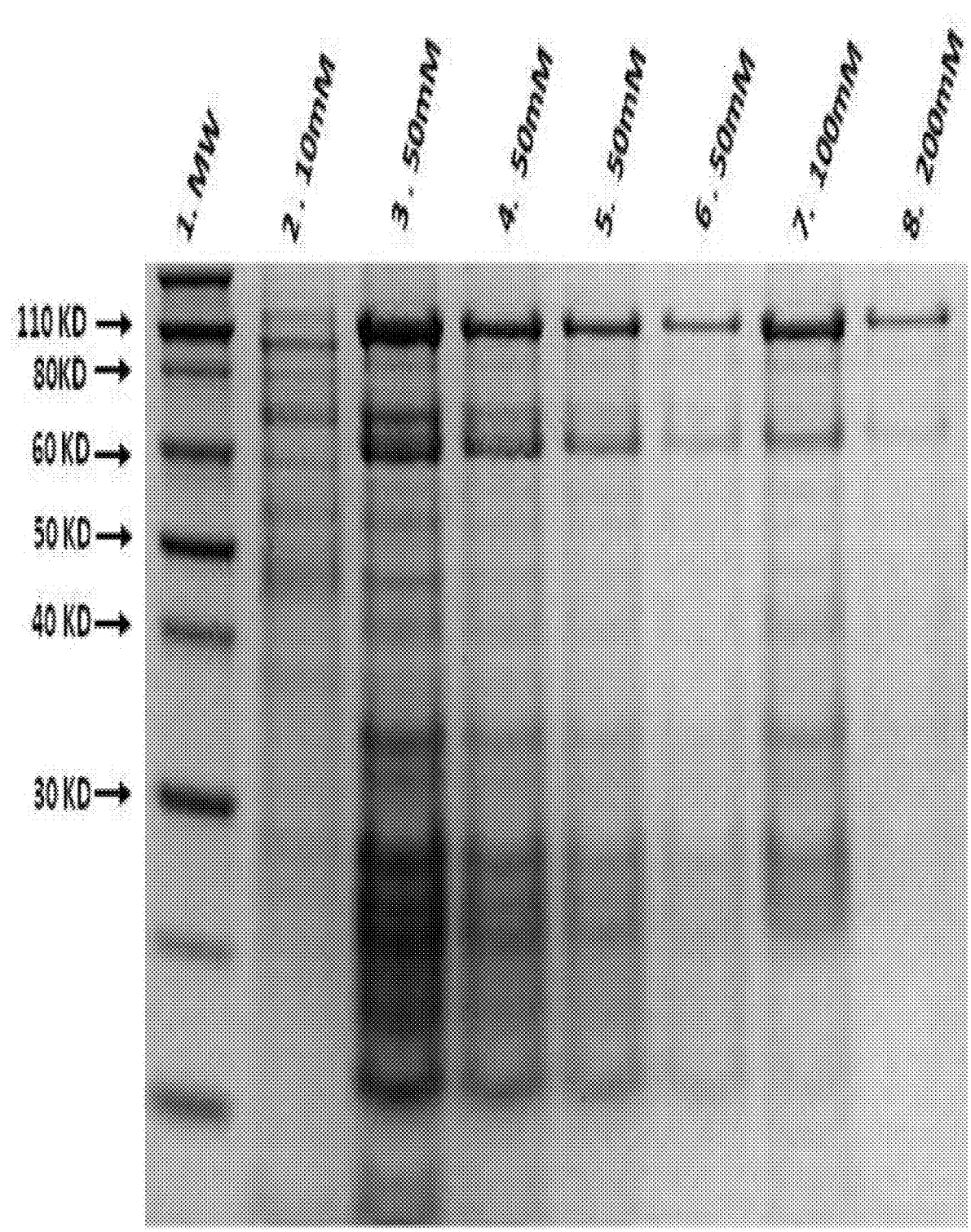
FIG. 3 shows the results of purification of recombinant TeNT heavy chain through $Ni^{2+}$-affinity column (Ni-NTA; Nickel-Nitrilotriacetic acid) chromatography.

Main object of the present invention is to provide a novel composition for the delivery of vaccine by oral or nasal administration.

Another object of present invention is to provide a novel composition for oral or nasal delivery of tetanus vaccine.

Yet another objective of present invention is to provide a novel composition for oral or nasal delivery of Tetanus, Diphtheria, and Pertussis Vaccine either alone or in combination thereof.

Another object of present invention is the use of neurotoxin associated protein (NAPs) for the oral or nasal delivery of the vaccine.

Another object of the present invention is the use of neurotoxin associated protein (NAPs) of *Clostridium botulinum*.

Yet another object of present invention is to provide a process for preparation of NAPs from type A *Clostridium botulinum*.

Yet another objective of present invention is to provide a process for the preparation of tetanus toxoid vaccine.

Yet another object of the present invention is to provide a process for the preparation of tetanus toxoid vaccine.

Yet another object of present invention is to provide first and second-generation process for the preparation of tetanus toxoid vaccine.

Yet another object of the present invention is to provide a process for the third-generation tetanus vaccine as Detoxified recombinant tetanus neurotoxin (DrTeNT). DrTeNT amino acid sequence is submitted as Sequence ID No. 1 (SEQ ID NO: 1).

Yet another object of present invention is to provide a testing model for the effectiveness of the oral and intranasal delivery of the vaccine.

Yet another object of present invention is to provide a testing model in rabbit or another suitable model for the effectiveness of the oral and intranasal delivery of the vaccine.

Another object of the present invention is oral or nasal delivery of vaccine.

Yet another object of the present invention is oral or nasal delivery of Tetanus, Botulinum, Diphtheria, and Pertussis Vaccine either alone or in combination thereof.

Another object of the present invention is to provide process for preparation of composition for the vaccine.

BRIEF SUMMARY OF THE INVENTION

Accordingly, the present invention provides a composition of neurotoxin associated proteins and vaccine.

Another embodiment of the present invention is wherein the neurotoxin associated proteins (NAPs) is of botulinum neurotoxin.

Another embodiment of the present invention is wherein the neurotoxin associated proteins (NAPs) are used as a delivery vehicle for tetanus vaccine delivery.

Another embodiment of the present invention is wherein the vaccine is selected from the group consisting of tetanus, diphtheria and pertussis alone, or any combination thereof.

Another embodiment of the present invention is wherein the tetanus vaccine is a non-toxic protein domain of TeNT.

Another embodiment of the present invention, is wherein the non-toxic protein domain of TeNT is selected from the heavy (H) chain or detoxified recombinant TeNT (DrTeNT) alone, or in combination thereof.

Another embodiment of the present invention, is wherein the detoxified recombinant TeNT (DrTeNT) is selected from mutated light chain or native heavy chain, or a combination thereof.

Another embodiment of the present invention is wherein the vaccine is made of a fusion with DrTeNT or any of its derived fragments with a diphtheria vaccine element.

Another embodiment of the present invention is wherein vaccine DrTeNT is combined with pertussis vaccine element as a fusion protein.

Another embodiment of the present invention is wherein vaccine DrTeNT is combined with vaccine elements of diphtheria and pertussis vaccine elements as a fusion protein.

A further embodiment of the present invention is a process for the preparation of second-generation tetanus toxoid vaccine, i.e., tetanus heavy chain comprising the steps of;
  a. Induction of *E. coli* culture $OD_{600}$=0.5 by adding 0.2 mM isopropyl β-D-1-thiogalactopyranoside or isopropylthio-β-galactoside, (IPTG);
  b. Growing culture for 14-16° C. for 14 to 20 hours;
  c. the cell paste suspends in 25 mM phosphate buffer containing 200 mM sodium chloride;
  d. add 1% of TRITON®-X-100 to the phosphate buffer;
  e. Sonicate for a period of 3 minutes (3-5 sec on/off pulse) at 4° C. on cold beads;
  f. Centrifuge the culture for 60 to 90 minutes;
  g. Supernatant is collected;
  h. Supernatant purified using Ni-NTA affinity column; and
  i. Combine the pool which has less contaminated bands and concentrate the pool by using CENTRIPREP®-30.

Another embodiment of the present invention, wherein in the process, the pH of the buffer is in the range of 7.2 to 8.0.

Another embodiment of the present invention, wherein in the process, the pH of the buffer is preferably 7.4.

Another embodiment of the present invention, wherein in the process, the rpm of the centrifuge rotation is 8000-15000 rpm per hour for 45 to 90 minutes.

Another embodiment of the present invention, wherein the eluent is imidazole solution.

Yet another embodiment of the present invention, wherein the concentration of imidazole solution is 10 mM, 50 mM, 100 mM, 200 mM and 500 mM.

Accordingly, the present invention relates a process for preparation of third-generation detoxified recombinant tetanus toxoid vaccine comprising the steps of:
  a. pBN3 vector was used for cloning TeTx Light chain in a BL21(DE3) strain for expression of the plasmid;
  b. Two active sites mutation, E234A and E271A, was done which corresponds to E224 and E262 of BoNT/A active sites;
  c. HC portion of TeNT was fused to construct full length tetanus neurotoxin plasmid with two active sites mutation, E234A and E271A; and
  d. Purified the large band at 150 kDa protein position using Ni-NTA affinity column.

Yet another embodiment of the present invention comprises a process wherein the strain used for expression of the plasmid *E. coli* BL21 (DE3).

Yet another embodiment of the present invention is a process wherein a purified large band at 150 kDa protein is obtained as soluble and stable.

Accordingly, the present invention relates to a process for the preparation of vaccine and NAPs composition comprises:
  a. mixing equimolar ratio of vaccine and NAPs at pH 5.5 to 6.2;
  b. reacting at an ambient temperature for 2-3 hours;
  c. 25 mM phosphate buffer of pH 5.8 containing 200 mM sodium chloride solution charged to step b;
  d. reacting above obtained reaction mixture with 10 mM imidazole solution;
  e. loading the reaction mixture further to a G-100 column; and
  f. eluting the column to get the pure NAPs-vaccine composition.

Yet another embodiment of the present invention is a process wherein a vaccine is selected from the group consisting of tetanus, diphtheria, pertussis alone or combination thereof.

Yet another embodiment of the present invention is a process, wherein the temperature is in range of 20-30° C.

Yet another embodiment of the present invention is a process where the preferred pH is 5.8.

Yet another embodiment of the present invention is a process wherein the tetanus vaccine is a non-toxic protein domain of TeNT.

Yet another embodiment of the present invention is a process wherein the tetanus vaccine is selected from heavy (H) chain or detoxified recombinant TeNT (DrTeNT) alone or a combination thereof.

Yet another embodiment of the present invention is a process wherein, detoxified recombinant TeNT is selected from a mutated light chain or a native heavy chain or a combination thereof.

Yet another embodiment of the present invention is a process wherein NAPs are from botulinum neurotoxin.

Yet another embodiment of the present invention is a process wherein the NAPs are obtained from any serotype of *C. botulinum*.

Yet another embodiment of the present invention is a process wherein tetanus vaccine is linked to detoxified botulinum neurotoxin (DrBoNT).

Yet another embodiment of the present invention is a process wherein tetanus vaccine is linked to a fragment of detoxified botulinum neurotoxin.

Yet another embodiment of the present invention is a process wherein tetanus vaccine is linked to NAPs of botulinum neurotoxin.

Yet another embodiment of the present invention is the composition is used for the oral or nasal delivery of a vaccine.

Yet another embodiment of the present invention is the vaccine is selected from the group consisting of tetanus, diphtheria or pertussis alone or in combination thereof.

Yet another embodiment of the present invention is the tetanus vaccine is non-toxic protein domain of TeNT.

Yet another embodiment of the present invention is the non-toxic protein domain of TeNT is selected from a heavy (H) chain or a detoxified recombinant TeNT (DrTeNT) alone or in combination thereof.

Yet another embodiment of the present invention is the detoxified recombinant TeNT (DrTeNT) is selected from a mutated light chain or a native heavy chain or a combination thereof.

Yet another embodiment of the present invention is the vaccine is made of a fusion with DrTeNT or any of its derived fragments with diphtheria vaccine element.

Yet another embodiment of the present invention is the DrTeNT is combined with pertussis vaccine element as a fusion protein.

Yet another embodiment is a vaccine, wherein DrTeNT is combined with vaccine elements of diphtheria and pertussis vaccine elements as a fusion protein.

DETAILED DESCRIPTION OF THE INVENTION

The present invention employs use of neurotoxin associated proteins (NAPs) of botulinum neurotoxin (BoNT) produced by *Clostridium botulinum* as a delivery vehicles of tetanus vaccine. BoNT is a food poison produced in the form of a complex with NAPs, which protect it from the low pH and proteases of the gastro-intestinal tract. In addition, NAPs are known to help in translocation of the BoNT across the mucosal layer of intestine as well as the nasal passage. Given the similarity of structure of BoNT and TeNT and their common mode of action, NAPs bind and protect and translocate a tetanus vaccine across the mucosal layer.

*Clostridium botulinum* produces seven serotypes of botulinum neurotoxins (A-G). It is basically made of two protein chains one is 100 kDa polypeptide heavy chain and another is 50 kDa polypeptide light chain bridged through disulphide link. Botulinum neurotoxins is synthesized in a complex form, in which neurotoxin is surrounded by several non-toxin proteins known as neurotoxin associated proteins (NAPs). NAPs have been shown to have two major roles in the intoxication process of botulism. The first role is the assistance of NAPs in the translocation of the BoNT across the intestinal mucosal layer. The second role is NAPs protect the BoNT against acidity and proteolytic attack of the enzymes of gastric juice. Therefore it becomes a perfect delivery system for vaccine. The TeNT, having over 35% sequence homology with BoNTs, and sharing much of the structural and functional features of BoNT, but is not a food poison due to the lack of NAPs. NAPs from one serotype of BoNT bind and protect another serotype of BoNT, thus these can also bind, protect and deliver vaccines, specially TeNT or TeNT vaccine due to sequence homology and common structural and functional domains. Therefore, the present invention uses BoNT's NAPs for oral and intranasal delivery of vaccines, specially tetanus vaccine.

Botulinum and tetanus neurotoxins have several common features including over 35% sequence homology, and antagonistic effects of heterologous protein fragments. Both the neurotoxins have similar secondary structural contents, and both have their 'catalytic domain' light chain on the C-terminal of their amino acid sequence. Tetanus is capable of causing botulism symptoms at high concentrations and blocks the release of acetylcholine from the presynaptic membranes just like the BoNT.

Similar mechanism of action for botulinum and tetanus neurotoxins at the molecular level occurs. Experimental studies reveal many similarities between the two neurotoxins including the membrane channel formation by the N-terminal fragments of their respective heavy chains and blockage of the neurotransmitter release from cultured cells and proteolytic activity against synaptobrevin-2. It is believed that there is enough common structural and functional similarity between BoNT and TeNT. The botulinum NAPs bind and protect TeNT similar to BoNT/A, providing basis for NAPs use an oral carrier of vaccine, specially tetanus vaccine.

Figures 1, 2:
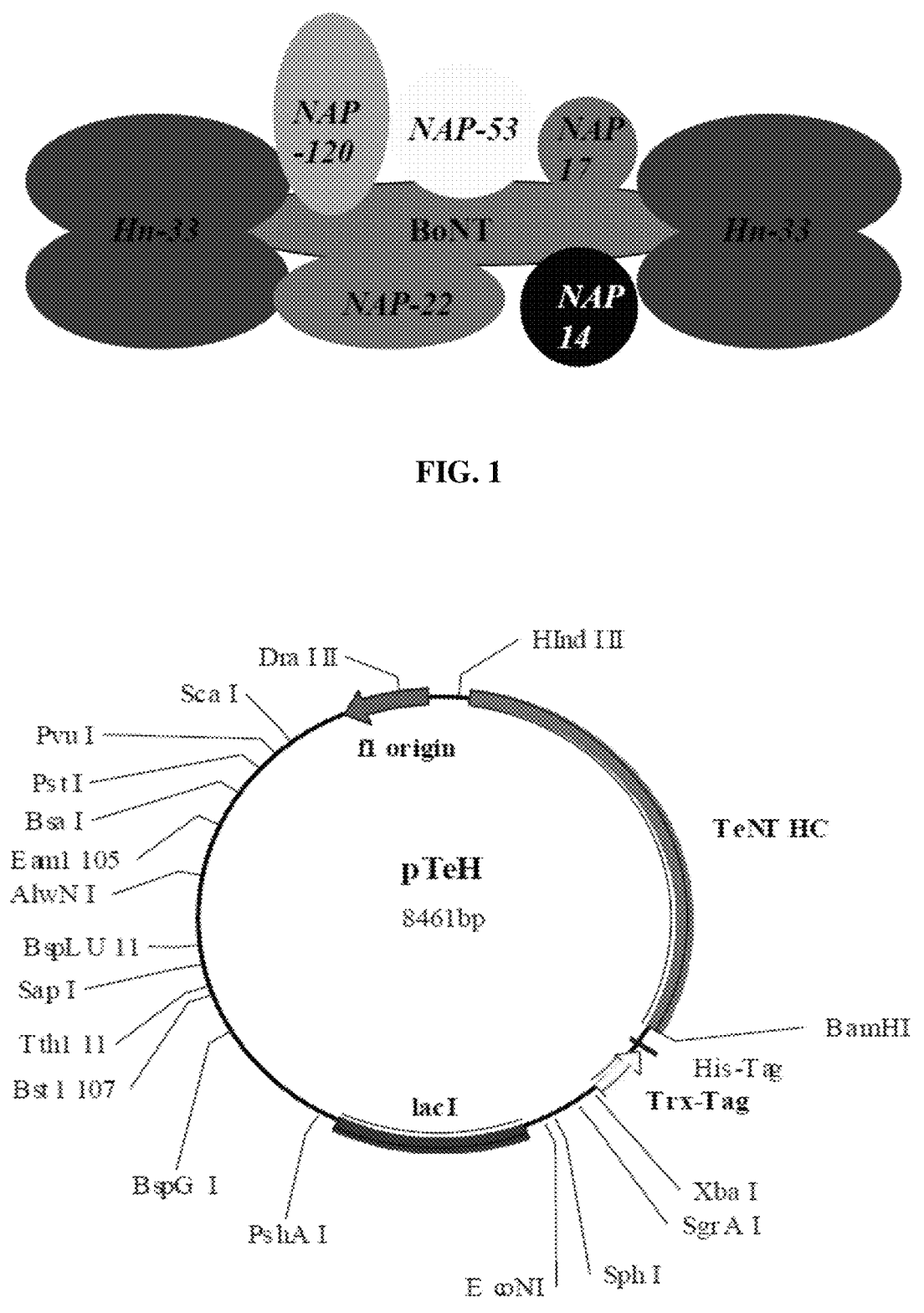

BoNT is a food poison produced in the form of a complex with NAPs (see FIG. 1). NAPs protect BoNT from the low pH and proteases of the gastro-intestinal tract (Mahmut et al., 2002). NAPs are known to help translocate the BoNT across the mucosal layer of intestine as well as the nasal passage (Fujinaga et al., 2004). Given the similarity of structure of BoNT and TeNT and their common mode of action, Hn-33 is likely to bind and protect and translocate a tetanus vaccine across the mucosal layer (Mahmut et al., 2002).

Due to 35% sequence homology, and antagonistic effects of heterologous protein fragments, there is evidence for strong common structural features. Also, the ability of tetanus for causing botulism symptoms at high concentrations just like the BoNT it is likely that these proteins have a similar mechanism of action for botulinum and tetanus neurotoxins at the molecular level. Experimental studies revealed many similarities between the two neurotoxins including the membrane channel formation by the N-terminal fragments of their respective heavy chains and blockage of the neurotransmitter release from cultured cells and proteolytic activity against synaptobrevin-2. Therefore, there is enough common structural and functional similarity between BoNT and TeNT that NAPs of BoNT/A NAPs will bind and protect TeNT similar to BoNT/A, which provides basis for NAPs use an oral carrier of vaccines, especially tetanus vaccine.

The Tetanus toxoid vaccine, a second-generation vaccine is prepared based on the non-toxic protein domain of TeNT, such as the heavy (H) chain for demonstrating its binding and delivery by NAPs.

The first steps include the preparation of a second-generation tetanus vaccine based on the non-toxic heavy chain of the TeNT. FIG. 2 shows the schematic genomic map of pET32a, showing the location of TeNT heavy chain TeNT heavy chain plasmids were transferred to BL21(DE3) competent cells, and grown in the LB media. The *E. coli* culture was induced at $OD_{600}$=0.5 by adding 0.2 mM IPTG and after induction culture continually grew at 16° C. for about 16 hours.

The second step is the preparation of NAPs from type A *Clostridium botulinum*.

Finally, demonstration of NAPs binding to the second-generation tetanus vaccine.

The present invention also provides a method of preparation of the clone of DrTeNT as the third-generation tetanus vaccine.

The third-generation tetanus vaccine is prepared from and/or detoxified recombinant TeNT (DrTeNT) is cloned in pET32a vector between BamHI and HindIII sites with the N-terminal his-tag.

We also demonstrate protection of vaccine by NAPs against low pH and gastric protease, and further demonstration of the oral and intranasal delivery of the tetanus vaccine in rabbits (FIG. 12) by evaluating protection against challenge with TeNT, and this allows one to compare the results with those obtained by intramuscular injections. Next, in this preferred embodiment, one may develop a primate model for testing the effectiveness of the oral and intranasal delivery of tetanus vaccine by NAPs as an initial step towards testing this needle free delivery system in humans.

Preparation of NAPs from Botulinum Neurotoxin

Botulinum neurotoxin and purification of NAPs is done as per known method in the art (Kukreja et al., Toxicon, 2009 (53) 616-624).

Preparation of Tetanus Toxoid Vaccine

In this preferred embodiment, the cell paste culture suspended in about 1 L, 25 mM phosphate buffer, pH 7.4, containing 200 mM sodium chloride and 1% of TRITON®-X-100—a nonionic surfactant otherwise known by its IUPAC name of 2-[4-(2,4,4-trimethylpentan-2-yl)phenoxy] ethanol—is added in the buffer (called basic buffer). After sonication, the cell lysate was centrifuged at 12,000 rpm for about 1 hour by using Thermo Scientific® Sorvall® Legend® RT Centrifuge and FIBERLite® F15-8×50C rotor, and then the supernatant is poured into a clean tube. The extract is thus obtained and is loaded to the pre-equilibrated Ni-NTA column.

After loading to the Ni-NTA affinity column, 10 mM imidazole is added to the basic buffer as a washing step, then protein binding to the column is eluted step by step at 50 mM imidazole, 100 mM imidazole, 200 mM imidazole and 500 mM imidazole. Next, one should combine the pool which has less contaminated bands and concentrate the pool by using CENTRIPREP®-30, or similar centrifugal filters that are disposable ultrafiltration devices used for purifying, concentrating, and desalting biological samples in the 2-15 mL volume range, and with a pore size of about 30 kDa. After concentration, measure the protein concentration by UV, then prepare to do further binding experiments with NAPs.

Purification results of TeNT heavy chain obtained in this embodiment are shown in FIG. 3.

Preparation of Detoxified Recombinant TeNT

The detoxified recombinant TeNT (DrTeNT) was prepared by cloning the TeNT gene and mutating two active site glutamic amino acid residues, E234 and E271 each to alanine residues. Cloning of Dr TeNT involved three steps: (1) pBN3 vector was used for cloning TeTx Light chain. (2) Two active sites mutation, E234A and E271A, was done which corresponds to E224 and E262 of BoNT/A active sites. (3) HC portion of TeNT was fused to construct full length tetanus neurotoxin plasmid with two active sites mutation, E234A and E271A.

E. coli BL21 (DE3) was used for the protein expression vector. After induction there were a large band at 150 kDa position which was the size of full-length recombinant tetanus neurotoxin. After Ni-NTA affinity column, about 5 mg/ml pure protein was obtained which was soluble and stable.

FIG. 3 shows the results of purification of recombinant TeNT heavy chain through $Ni^{2+}$-affinity column chromatography. Lane 1 is MW standards. Lane 2 is Ni-NTA (Nickel-Nitrilotriacetic acid) affinity column washing with 10 mM imidazole added in the basic buffer. Lanes 3-6 are elution with 50 mM imidazole concentration. Lane 7 is elution with 100 mM Imidazole. Lane 8 is elution with 200 mM imidazole.

Preparation of NAPs-Tetanus Heavy Chain Composition

In another preferred embodiment, tetanus heavy chain has N-terminal his-tag which can bind to Ni-NTA affinity column, but NAPs which is purified from botulinum neurotoxin complex cannot bind to the Ni-NTA affinity column, so pull down assay is used for analysis to demonstrate if heavy chain would bind with NAPs. If Heavy chain has interaction with NAPs, both HC and NAPs would remain bound to NTA column and will be released together from Ni-NTA affinity column after eluting with imidazole.

Approximately equal molar ratio of tetanus heavy chain and NAPs are mixed together at pH 5.8. Binding reaction is carried out at room temperature for 2 hours. 25 mM phosphate buffer, pH 5.8, containing 200 mM NaCl is used for procedure of pull-down assay. After reaction, the reaction mixture is diluted to a final imidazole concentration lower than 5 mM. The reaction mixture is loaded to the Ni-NTA affinity column, and 10 mM imidazole is added to the basic buffer to wash column at 20× bed volume, then the protein is eluted stepwise with 50 mM, 100 mM, 200 mM, 500 mM imidazole. The eluents are examined with SDS-PAGE to check the purity and intactness of the TeNT heavy chain, as illustrated in FIG. 3.

Tetanus heavy chain purified from different batches is used for the binding experiments. After HC and NAPs reaction at room temperature, reaction mixture is reloaded to the Ni-NTA affinity column, with 10 mM Imidazole added to the basic phosphate buffer for washing column. After then protein is eluted with 50 mM, 100 mM, 200 mM imidazole. From the gel, it was observed that Tetanus heavy chain and NAPs were eluted together at 50 mM imidazole concentration (FIG. 4).

Figure 4:
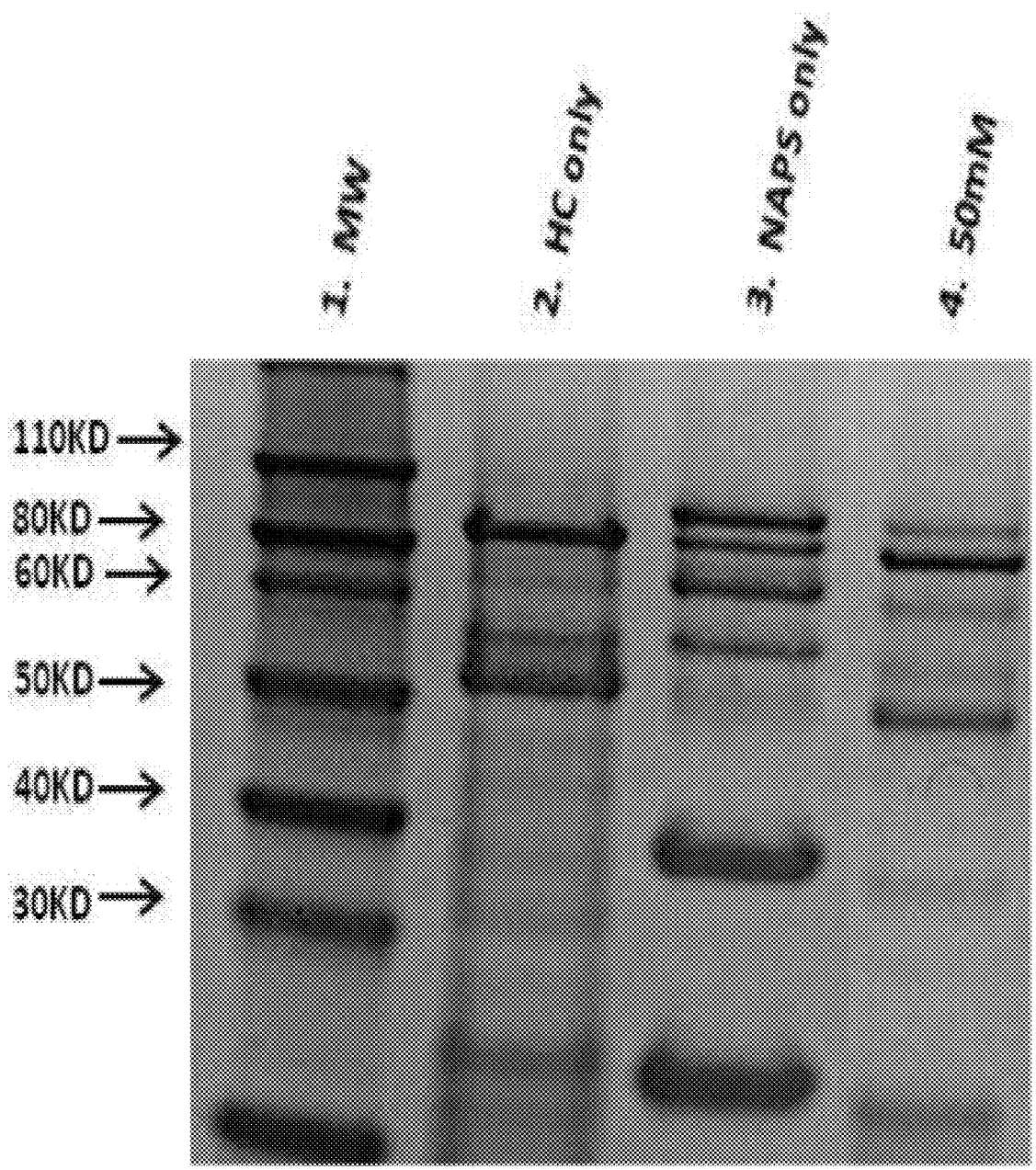
FIG. 4 shows the results of binding of recombinant tetanus heavy chain (HC) preparation with NAPs as analyzed on $Ni^{2+}$-affinity column chromatography.

FIG. 4 shows binding of recombinant tetanus heavy chain (HC) preparation with NAPs as analyzed on $Ni^{2+}$-affinity column chromatography. Lane 1 is MW. Lane 2 is intact heavy chain protein. Lane 3 is intact NAPs. Lane 4 is elution from Ni-NTA affinity column with imidazole 50 mM after loading HC and NAPs reaction mixture to Ni-NTA affinity column, Lane 4 showed HC and NAPs came together at 50 mM imidazole concentration.

NAPs results shown in FIG. 4, lane 4, demonstrating that the NAPs successfully bound to the tetanus heavy chain. This observation would suggest that the tetanus heavy chain could be carried through the digestive system when administered orally in combination with NAPs. The NAPs are also expected to deliver the tetanus heavy chain or whole tetanus toxin across the intestinal mucosal layer.

Binding between tetanus heavy chain and NAPs is therefore demonstrated. Prepared clone of detoxified recombinant TeNT or DrTeNT which is full length TeNT with only two active site amino acid residues mutated (FIG. 5 and FIG. 6) has been achieved. DrTeNT has been successfully cloned in a pBN3 vector between E.coRI and PstI sites with C-terminal his-tag. The schematic diagram of new vector construct, named pDrT vector, is shown in FIG. 7.

Figure 5A:
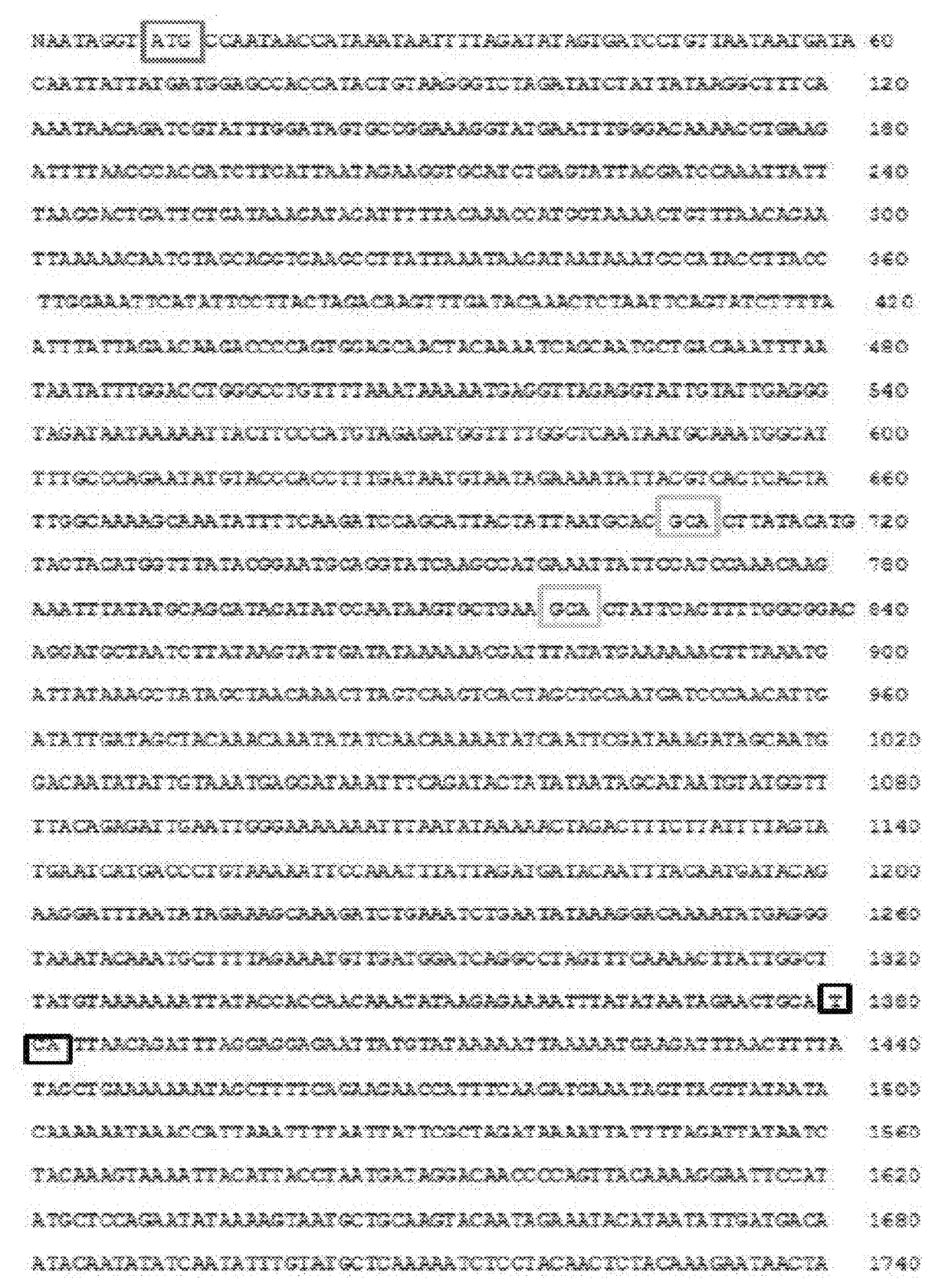

FIG. 5 shows nucleotide sequence of DrTeNT (3951 bp, including stop codon) which encodes for the full length double mutant tetanus gene. The start codon is enclosed in a green box, which is the same start for TeNT light chain; the double mutation sites are enclosed in orange boxes, GAA (Glu) to GCA (ALA) mutation; the heavy chain start codon (TCA) is enclosed in black box; and the stop codon is enclosed in a red box following the six His tag.

Figure 6B:
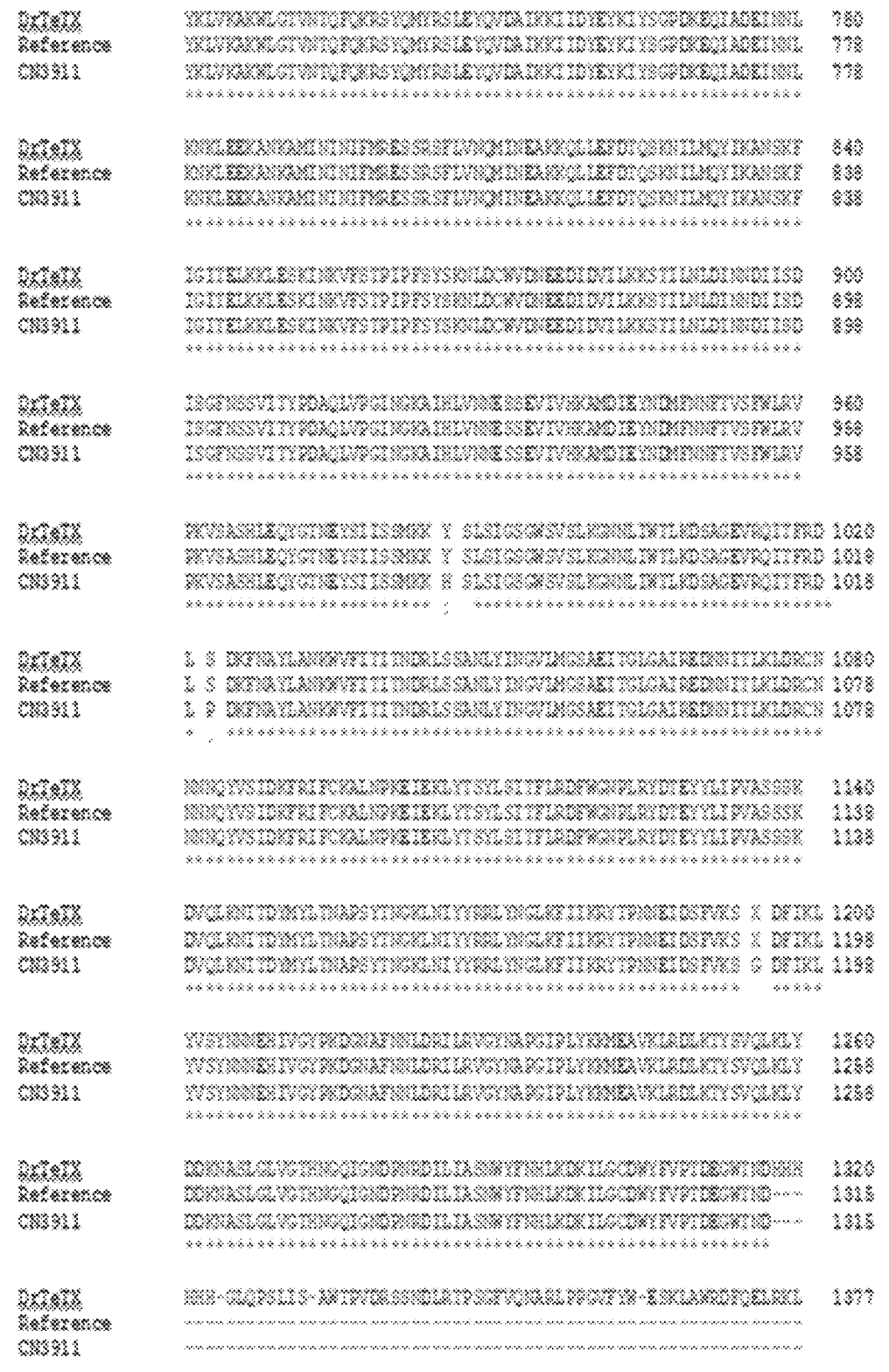

FIG. 6 shows the amino acid sequence alignment of DrTeNT, reference (data from wildtype genomic DNA), and CN3911 from Genebank. The two red boxes show that two active sites which got mutated in DrTeNT from wild type. The black boxes show that amino acid sequence variation from GeneBank *C. tetani* strain.

Figure 7:
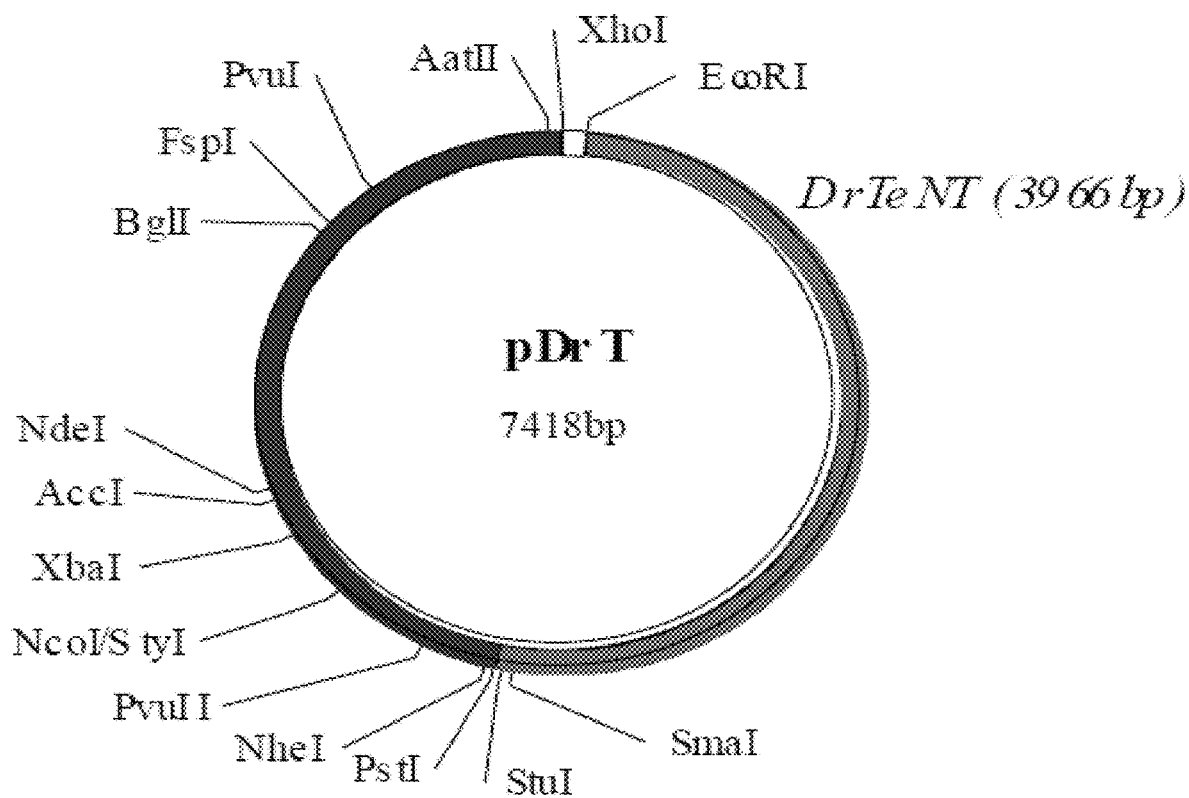
FIG. 7 shows a schematic representation of pDrT vector map containing DrTeNT gene, shown in grey color (3966 bp include 6-His tag).

FIG. 7 shows a schematic representation of pDrT vector map containing DrTeNT gene (3966 bp include 6-His tag). DrTeNT was cloned in pBN3 vector (3452 bp), between E.coRI and PstI sites. The new construction of pDrT vector is 7418 bp in length.

Figure 8A:
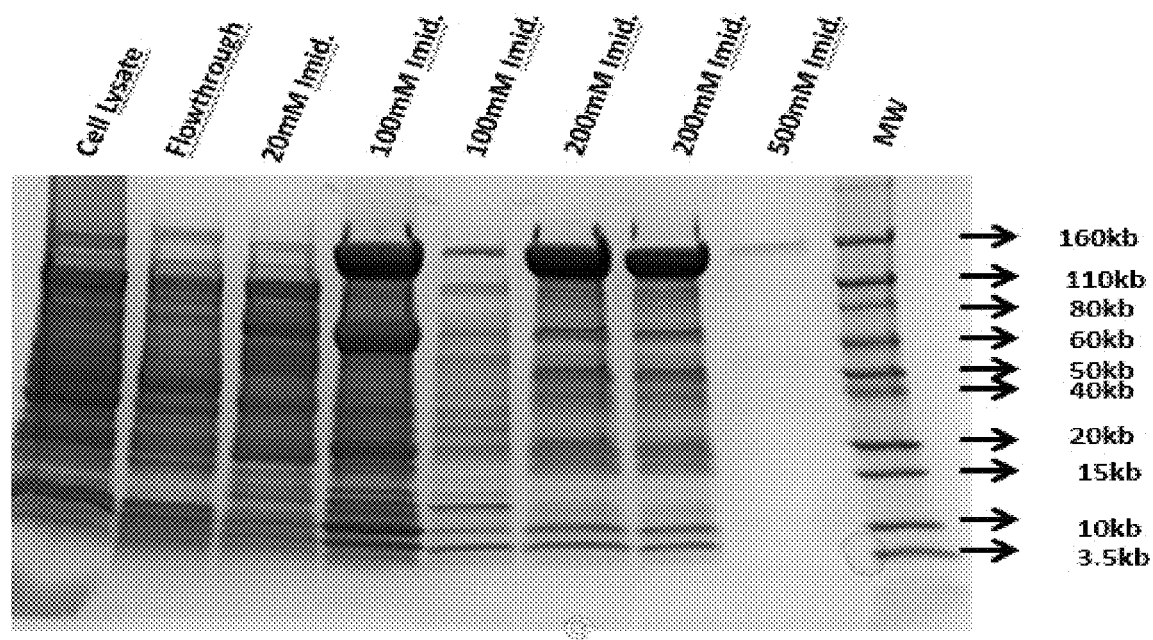
FIGS. 8A-8B shows TeNT protein purification process and the end product.
Figure 8B:
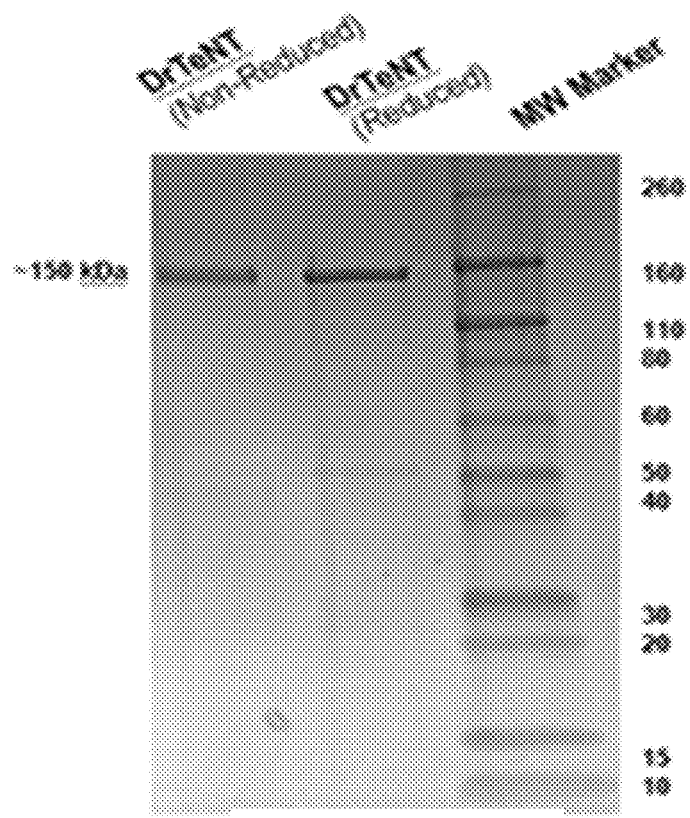

Expression of DrTeNT gene in *E. coli* has been achieved and better than 99% pure DrTeNT is purified on a Ni-NTA affinity column (FIG. 8).

Figure 9:
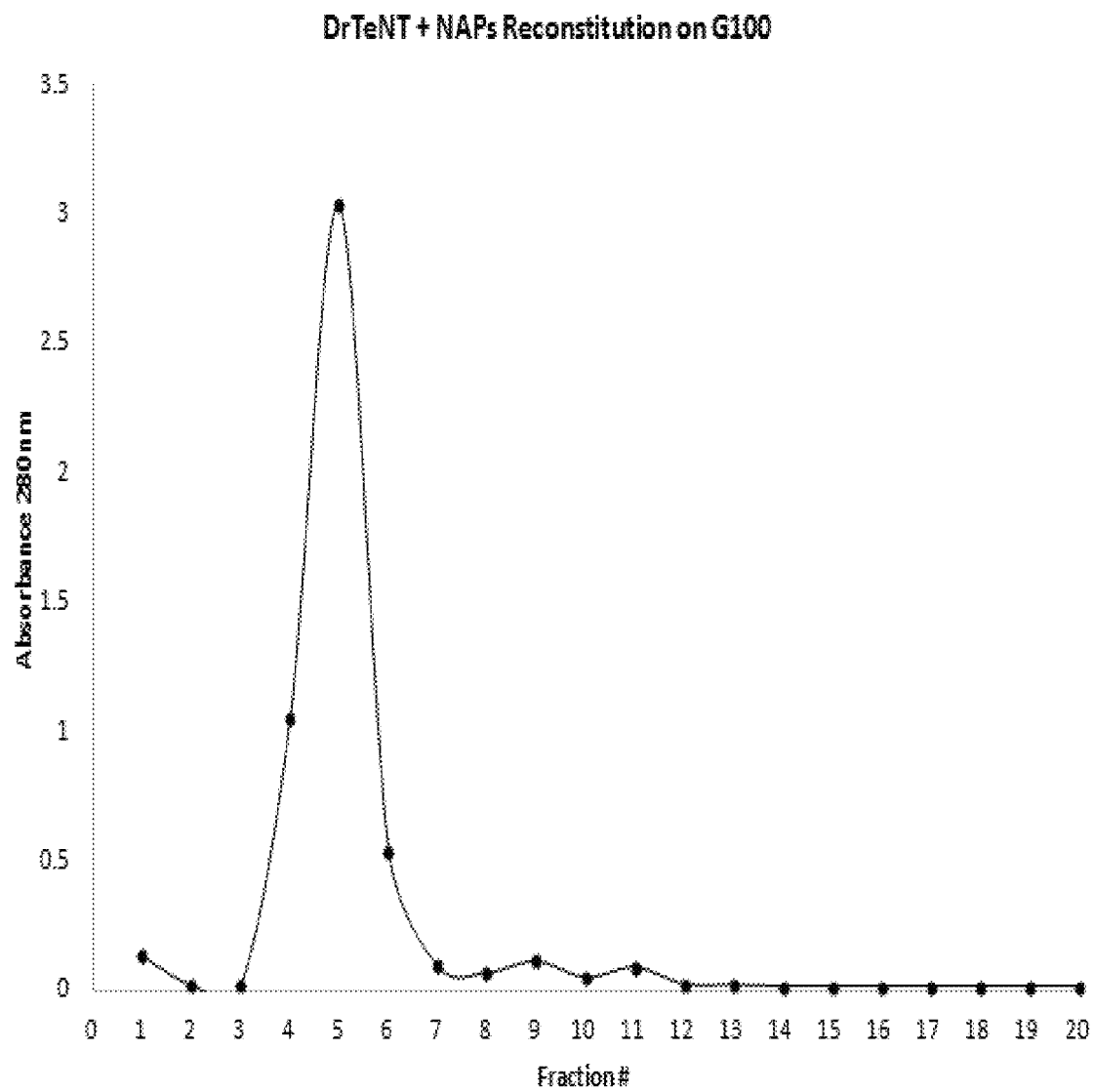
FIG. 9. Binding of NAPs and DrTeNT is demonstrated using a G-100 gel filtration column chromatography performed in 50 mM sodium phosphate buffer, pH 5.8, containing 200 mM NaCl, showing a single peak elution of the mixture containing all the NAPs and DrTeNT.
Figure 10:
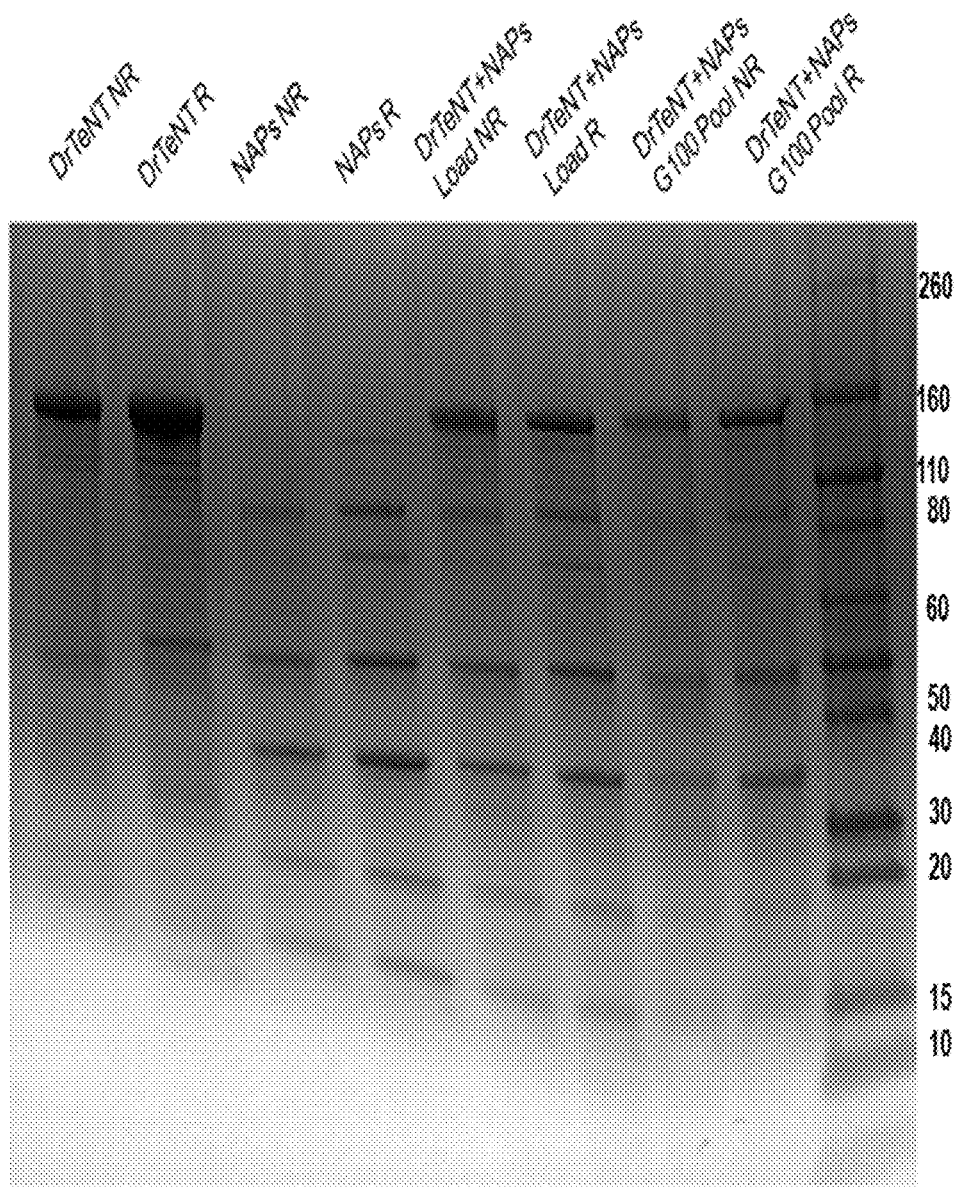
FIG. 10. SDS-PAGE analysis of DrTeNT, NAPs, DrTeNT+NAPs load to the G-100 column, and DrTeNT+NAPs elution pool from the G-100 gel filtration column.
Figure 11:
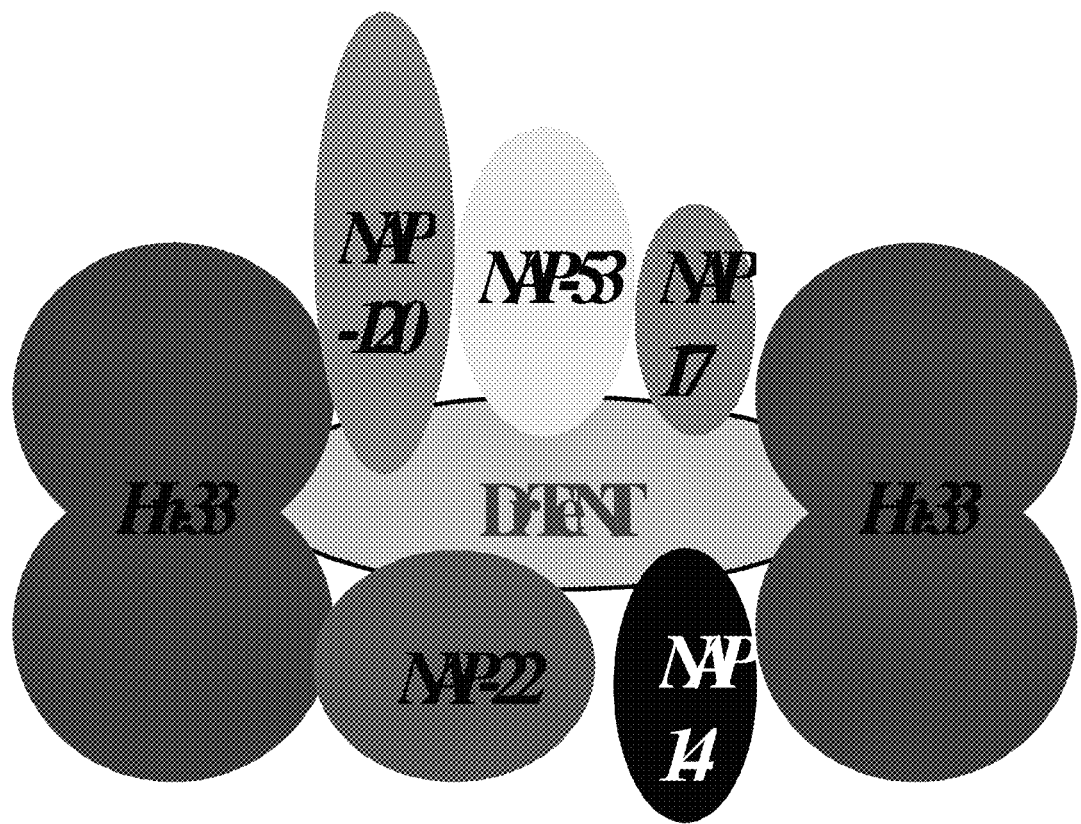
FIG. 11. Schematic model of the DrTeNT-NAPs complex.

Binding of NAPs and DrTeNT is demonstrated using a G-100 gel filtration column chromatography performed in 50 mM sodium phosphate buffer, pH 5.8, containing 200 mM NaCl, showing a single peak elution of the mixture containing all the NAPs and DrTeNT (FIG. 9). Binding of NAPs and DrTeNT is confirmed by SDS-PAGE gel (FIG. 10). A model of the DrTeNT and NAPs complex is shown in FIG. 11.

In another preferred embodiment the binding of the NAPs to tetanus heavy chain or DrTeNT is done using high-performance liquid chromatography (HPLC). In this preferred embodiment both NAPs and HC (used as a control) run separately when passed through the size exclusion column. After mixing them together at low pH conditions for binding with each other, and the mixture will appear as a single elution band.

In another preferred embodiment the binding of the NAPs to tetanus heavy chain is done using enzyme-linked immunosorbent assay (ELISA). In this preferred embodiment the tetanus heavy chain is coated on the 96 well plate at various different concentration Incubation of NAPs labelled with Horseradish Peroxidase (HRP) will show concentration dependent binding as monitored by colorimetric method by adding HRP substrate.

In another preferred embodiment the binding of the NAPs to tetanus heavy chain or DrTeNT is done using a BIA-CORE® surface plasmon resonance. In this preferred embodiment binding is evaluated on a gold chip.

In another preferred embodiment the binding of the NAPs to tetanus heavy chain or DrTeNT is done using isothermal calorimetry. In this preferred embodiment titration of a given concentration of NAPs with varying concentrations of tetanus vaccine candidate will show changes in heat evolved, thus allowing calculation of binding constant.

In another preferred embodiment the binding of the NAPs to tetanus heavy chain or DrTeNT is done using Fluorescence anisotropy. In this preferred embodiment the tetanus vaccine candidate can be labelled with a fluorescent probe, and titrated with the NAPs by monitoring fluorescence anisotropy.

In another preferred embodiment the binding of the NAPs to tetanus heavy chain, DrTeNT, or any other fragment thereof is demonstrated with x-ray crystallography.

In another preferred embodiment the binding of the NAPs to tetanus heavy chain or DrTeNT is demonstrated with electron microscopy.

In another preferred embodiment the binding of the NAPs to tetanus heavy chain, DrTeNT, or any other fragment thereof is demonstrated with NMR spectroscopy.

In another preferred embodiment the binding of the NAPs to tetanus heavy chain, DrTeNT, or any other fragment thereof is demonstrated with molecular dynamic simulations.

In another preferred embodiment the binding of the NAPs to tetanus heavy chain, DrTeNT, or any other fragment thereof is demonstrated with circular dichroism spectroscopy.

In another preferred embodiment the binding of the NAPs to tetanus heavy chain, DrTeNT, or any other fragment thereof is demonstrated with FTIR spectroscopy.

Evaluation of the Oral Delivery of Tetanus Vaccine

Figure 12:
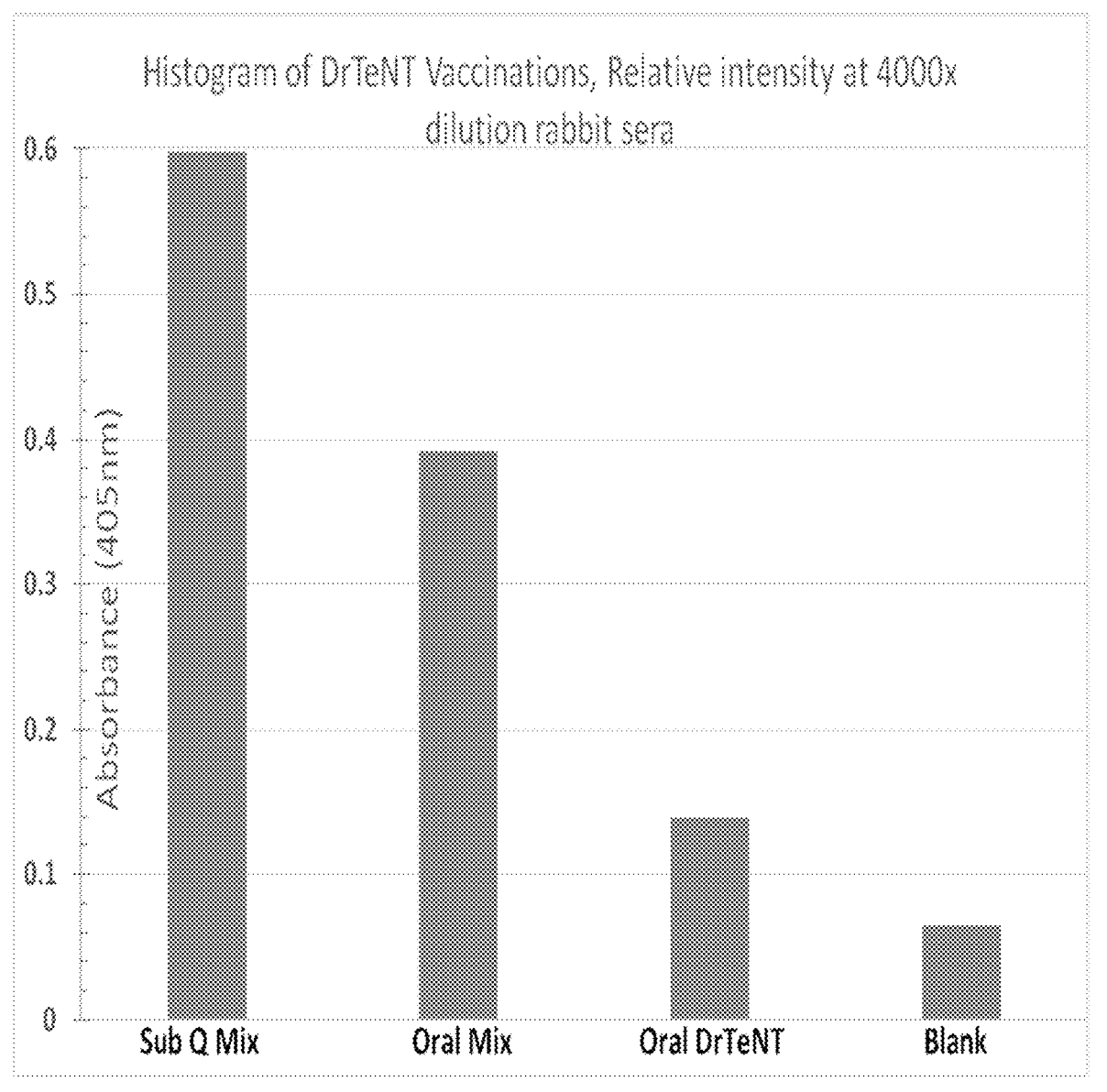

The effectiveness of inducing an immune response with oral delivery as well as subcutaneous delivery is shown in FIG. 12. The first bar Sub Q Mix is subcutaneous mixture of NAPs with DrTeNT, next bar is same material via oral root and then oral DrTeNT alone. Although subcutaneous is more effective to illicit a response it seem that via oral mixture of both articles are more effective than the DrTeNT alone.

In another preferred embodiment neurotoxin associated protein from botulinum neurotoxin complex used as a delivery system for a tetanus vaccine.

In another preferred embodiment a neurotoxin associated protein from botulinum neurotoxin used as a delivery system for a tetanus vaccine.

In another preferred embodiment the tetanus heavy chain is used.

In another preferred embodiment the tetanus heavy chain linked to a botulinum toxin fragment is used.

In another preferred embodiment DrTeNT linked to DrBoNT is used.

In another embodiment a neurotoxin associated protein from botulinum neurotoxin complex is used as delivery system to botulinum vaccine.

In another embodiment neurotoxin associated proteins from botulinum neurotoxin complex is used as delivery system to botulinum vaccine.

In another embodiment, DrBoNT or any other fragment thereof is used as a vaccine.

In another preferred embodiment the neurotoxin associated protein is obtained from *Clostridium botulinum*.

In another preferred embodiment the neurotoxin associated protein is obtained from recombinant protein expression system.

In another preferred embodiment the neurotoxin associated protein is obtained from *Clostridium botulinum* bind to tetanus heavy chain.

In another preferred embodiment the detoxified recombinant form of whole tetanus neurotoxin (DrTeNT) containing mutated light chain and native heavy chain is used as vaccine alone for oral and intranasal delivery.

In another preferred embodiment the detoxified form of whole tetanus neurotoxin containing mutated light chain and native heavy chain is used as vaccine in combination with the neurotoxin associated protein for oral and intranasal delivery.

In another preferred embodiment the DrTeNT is combined with diphtheria vaccine element as a fusion protein.

In another preferred embodiment the DrTeNT is combined with pertussis vaccine element as a fusion protein.

In another preferred embodiment the DrTeNT is combined with vaccine elements of diphtheria and pertussis vaccine elements as a fusion protein.

In another preferred embodiment the group of neurotoxin associated proteins (NAPs) is used as a delivery vehicle for tetanus vaccine delivery.

In another preferred embodiment the tetanus vaccine is heavy chain of tetanus.

In another preferred embodiment the tetanus vaccine is light chain of tetanus.

In another preferred embodiment the tetanus vaccine is any fragment of tetanus.

In another preferred embodiment the vaccine is made of a fusion with DrTeNT or any of its derived fragments with diphtheria vaccine element.

In another preferred embodiment the vaccine is made of a fusion with DrTeNT or any of its derived fragments with pertussis vaccine element.

In another preferred embodiment the vaccine is made of a fusion with DrTeNT or any of its derived fragments with pertussis and diphtheria vaccine elements.

In another preferred embodiment the drug is created by combining DrTeNT or any of its fragments with any other drug candidate.

Applicant has described applicant's preferred embodiments of this invention, however it will be understood that the broadest scope of this invention includes modifications such as use of other equipment and laboratory procedures. Such scope is limited only by the claims as read in connection with the specification. Other advantages of the present invention will be apparent to those skilled in the art from the descriptions and the claims.

Advantages of the Invention

The present invention gives a novel composition of neurotoxin associated protein and vaccine.

The neurotoxin associated protein helps in oral or nasal delivery of vaccine, especially tetanus vaccine with or without diphtheria and pertussis.

Further, the present invention gives a novel process for the preparation of second and third generation of vaccine.

The present invention also provides a novel process for the preparation of composition of neurotoxin associated protein and vaccine for oral delivery or nasal delivery.

The present invention also provides a method for evaluation of the efficiency of the oral delivery of vaccine.

Trademarks: the product names used in this document are for identification purposes only; and are the property of their respective owners.

The term "about" as used herein refers to a value within 5% of the underlying parameter (i.e., plus or minus 1-5%).

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

What is claimed is:

1. A process for the preparation of a second-generation tetanus toxoid vaccine, comprising the steps of:
   a) inducing an *E. coli* culture at $OD_{600}$=0.5 by adding 0.2 mM isopropyl-β-D-1-thiogalactopyranoside (IPTG);
   b) growing the culture at 14-16° Celsius (C) for 14 to 20 hours;
   c) suspending the culture in 25 mM phosphate buffer containing 200 mM sodium chloride;
   d) adding 1% of (2-[4-(2,4,4-trimethylpentan-2-yl)phenoxy]ethanol) to the phosphate buffer and resuspending the culture in said phosphate buffer;
   e) sonicating the culture for a period of 3 minutes (at 5 sec on/off pulse) at 4° C. on cold beads;
   f) centrifuging the culture for 45 to 90 minutes;
   g) collecting and purifying the supernatant using Nickel-Nitrilotriacetic acid (Ni-NTA) affinity column with an eluant; and
   h) combining the eluant into a pool with contaminated bands and concentrating using centrifugal filters to isolate one or more detoxified domains of a tetanus neurotoxin (DrTeNT) heavy chains proteins.

2. The process of claim 1, wherein the pH of the buffer is in a range of 7.2 to 8.0.

3. The process of claim 1, wherein the pH of the buffer is 7.4.

4. The process of claim 1, wherein the centrifuging is performed at 8000-15000 rpm per hour for 45 to 90 minutes.

5. The process of claim 1, wherein the eluant is imidazole solution.

6. The process of claim 5, wherein the concentration of the imidazole solution is one of: 10 mM, 50 mM, 100 mM, 200 mM or 500 mM.

* * * * *

SEQUENCE LISTING

```
Sequence total quantity: 3
SEQ ID NO: 1            moltype = AA   length = 3945
FEATURE                 Location/Qualifiers
source                  1..3945
                        mol_type = protein
                        organism = Clostridium tetani
SEQUENCE: 1
METPROILET HRILEASNAS NPHEARGTYR SERASPPROV ALASNASNAS PTHRILEILE    60
METMETGLUP ROPROTYRCY SLYSGLYLEU ASPILETYRT YRLYSALAPH ELYSILETHR   120
ASPARGILET RPILEVALPR OGLUARGTYR GLUPHEGLYT HRLYSPROGL UASPPHEASN   180
PROPROSERS ERLEUILEGL UGLYALASER GLUTYRTYRA SPPROASNTY RLEUARGTHR   240
ASPSERASPL YSASPARGPH ELEUGLNTHR METVALLYSL EUPHEASNAR GILELYSASN   300
ASNVALALAG LYGLUALALE ULEUASPLYS ILEILEASNA LAILEPROTY RLEUGLYASN   360
SERTYRSERL EULEUASPLY SPHEASPTHR ASNSERASNS ERVALSERPH EASNLEULEU   420
GLUGLNASPP ROSERGLYAL ATHRTHRLYS SERALAMETL EUTHRASNLE UILEILEPHE   480
GLYPROGLYP ROVALLEUAS NLYSASNGLU VALARGGLYI LEVALLEUAR GVALASPASN   540
LYSASNTYRP HEPROCYSAR GASPGLYPHE GLYSERILEM ETGLNMETAL APHECYSPRO   600
GLUTYRVALP ROTHRPHEAS PASNVALILE GLUASNILET HRSERLEUTH RILEGLYLYS   660
SERLYSTYRP HEGLNASPPR OALALEULEU LEUMETHISG LULEUILEHI SVALLEUHIS   720
GLYLEUTYRG LYMETGLNVA LSERSERHIS GLUILEILEP ROSERLYSGL NGLUILETYR   780
METGLNHIST HRTYRPROIL ESERALAGLU GLULEUPHET HRPHEGLYGL YGLNASPALA   840
ASNLEUILES ERILEASPIL ELYSASNASP LEUTYRGLUL YSTHRLEUAS NASPTYRLYS   900
ALAILEALAA SNLYSLEUSE RGLNVALTHR SERCYSASNA SPPROASNIL EASPILEASP   960
SERTYRLYSG LNILETYRGL NGLNLYSTYR GLNPHEASPL YSASPSERAS NGLYGLNTYR  1020
ILEVALASNG LUASPLYSPH EGLNILELEU TYRASNSERI LEMETTYRGL YPHETHRGLU  1080
ILEGLULEUG LYLYSLYSPH EASNILELYS THRARGLEUS ERTYRPHESE RMETASNHIS  1140
ASPPROVALL YSILEPROAS NLEULEUASP ASPTHRILET YRASNASPTH RGLUGLYPHE  1200
ASNILEGLUS ERLYSASPLE ULYSSERGLU TYRLYSGLYG LNASNMETAR GVALASNTHR  1260
ASNALAPHEA RGASNVALAS PGLYSERGLY LEUVALSERL YSLEUILEGL YLEUCYSLYS  1320
LYSILEILEP ROPROTHRAS NILEARGGLU ASNLEUTYRA SNARGTHRAL ASERLEUTHR  1380
ASPLEUGLYG LYGLULEUCY SILELYSILE LYSASNGLUA SPLEUTHRPH EILEALAGLU  1440
LYSASNSERP HESERGLUGL UPROPHEGLN ASPGLUILEV ALSERTYRAS NTHRLYSASN  1500
LYSPROLEUA SNPHEASNTY RSERLEUASP LYSILEILEL EUASPTYRAS NLEUGLNSER  1560
LYSILETHRL EUPROASNAS PARGTHRTHR PROVALTHRL YSGLYILEPR OTYRALAPRO  1620
GLUTYRLYSS ERASNALAAL ASERTHRILE GLUILEHISA SNILEASPAS PASNTHRILE  1680
TYRGLNTYRL EUTYRALAGL NLYSSERPRO THRTHRLEUG LNARGILETH RMETTHRASN  1740
SERVALASPA SPALALEUIL EASNSERTHR LYSILETYRS ERTYRPHEPR OSERVALILE  1800
SERLYSVALA SNGLNGLYAL AGLNGLYILE LEUPHELEUG LNTRPVALAR GASPILEILE  1860
ASPASPPHET HRASNGLUSE RSERGLNLYS THRTHRILEA SPLYSILESE RASPVALSER  1920
THRILEVALP ROTYRILEGL YPROALALEU ASNILEVALL YSGLNGLYTY RGLUGLYASN  1980
PHEILEGLYA LALEUGLUTH RTHRGLYVAL VALLEULEUL EUGLUTYRIL EPROGLUILE  2040
THRLEUPROV ALILEALAAL ALEUSERILE ALAGLUSERS ERTHRGLNLY SGLULYSILE  2100
```

-continued

```
ILELYSTHRI LEASPASNPH ELEUGLULYS ARGTYRGLUL YSTRPILEGL UVALTYRLYS   2160
LEUVALLYSA LALYSTRPLE UGLYTHRVAL ASNTHRGLNP HEGLNLYSAR GSERTYRGLN   2220
METTYRARGS ERLEUGLUTY RGLNVALASP ALAILELYSL YSILEILEAS PTYRGLUTYR   2280
LYSILETYRS ERGLYPROAS PLYSGLUGLN ILEALAASPG LUILEASNAS NLEULYSASN   2340
LYSLEUGLUG LULYSALAAS NLYSALAMET ILEASNGILEA SNILEPHEME TARGGLUSER  2400
SERARGSERP HELEUVALAS NGLNMETILE ASNGLUALAL YSLYSGLNLE ULEUGLUPHE   2460
ASPTHRGLNS ERLYSASNIL ELEUMETGLN TYRILELYSA LAASNSERLY SPHEILEGLY   2520
ILETHRGLUL EULYSLYSLE UGLUSERLYS ILEASNLYSV ALPHESERTH RPROILEPRO   2580
PHESERTYRS ERLYSASNLE UASPCYSTRP VALASPASNG LUGLUASPIL EASPVALILE   2640
LEULYSLYSS ERTHRILELE UASNLEUASP ILEASNASNA SPILEILESE RASPILESER   2700
GLYPHEASNS ERSERVALIL ETHRTYRPRO ASPALAGLNL EUVALPROGL YILEASNGLY   2760
LYSALAILEH ISLEUVALAS NASNGLUSER SERGLUVALI LEVALHISLY SALAMETASP   2820
ILEGLUTYRA SNASPMETPH EASNASNPHE THRVALSERP HETRPLEUAR GVALPROLYS   2880
VALSERALAS ERHISLEUGL UGLNTYRGLY THRASNGLUT YRSERILEIL ESERSERMET   2940
LYSLYSTYRS ERLEUSERIL EGLYSERGLY TRPSERVALS ERLEULYSGL YASNASNLEU   3000
ILETRPTHRL EULYSASPSE RALAGLYGLU VALARGGLNI LETHRPHEAR GASPLEUSER   3060
ASPLYSPHEA SNALATYRLE UALAASNLYS TRPVALPHEI LETHRILETH RASNASPARG   3120
LEUSERSERA LAASNLEUTY RILEASNGLY VALLEUMETG LYSERALAGL UILETHRGLY   3180
LEUGLYALAI LEARGGLUAS PASNASNILE THRLEULYSL EUASPARGCY SASNASNASN   3240
ASNGLNTYRV ALSERILEAS PLYSPHEARG ILEPHECYSL YSALALEUAS NPROLYSGLU   3300
ILEGLULYSL EUTYRTHRSE RTYRLEUSER ILETHRPHEL EUARGASPPH ETRPGLYASN   3360
PROLEUARGT YRASPTHRGL UTYRTYRLEU ILEPROVALA LASERSERSE RLYSASPVAL   3420
GLNLEULYSA SNILETHRAS PTYRMETTYR LEUTHRASNG LAPROSERTY RTHRASNGLY   3480
LYSLEUASNI LETYRTYRAR GARGLEUTYR ASNGLYLEUL YSPHEILEIL ELYSARGTYR   3540
THRPROASNA SNGLUILEAS PSERPHEVAL LYSSERXAAA SPPHEILELY SLEUTYRVAL   3600
SERTYRASNA SNASNGLUHI SILEVALGLY TYRPROLYSA SPGLYASNAL APHEASNASN   3660
LEUASPARGI LELEUARGVA LGLYTYRASN ALAPROGLYI LEPROLEUTY RLYSLYSMET   3720
GLUALAVALL YSLEUARGAS PLEULYSTHR TYRSERVALG LNLEULYSLE UTYRASPASP   3780
LYSASNALAS ERLEUGLYLE UVALGLYTHR HISASNGLYG LNILEGLYAS NASPPROASN   3840
ARGASPILEL EUILEALASE RASNTRPTYR PHEASNHISL EULYSASPLY SILELEUGLY   3900
CYSASPTRPT YRPHEVALPR OTHRASPGLU GLYTRPTHRA SNASP                  3945

SEQ ID NO: 2           moltype = AA  length = 4131
FEATURE                Location/Qualifiers
source                 1..4131
                       mol_type = protein
                       organism = Clostridium tetani
SEQUENCE: 2
ILEGLYMETP ROILETHRIL EASNASNPHE ARGTYRSERA SPPROVALAS NASNASPTHR    60
ILEILEMETM ETGLUPROPR OTYRCYSLYS GLYLEUASPI LETYRTYRLY SALAPHELYS   120
ILETHRASPA RGILETRPIL EVALPROGLU ARGTYRGLUP HEGLYTHRLY SPROGLUASP   180
PHEASNPROP ROSERSERLE UILEGLUGLY ALASERGLUT YRTYRASPPR OASNTYRLEU   240
ARGTHRASPS ERASPLYSAS PARGPHELEU GLNTHRMETV ALLYSLEUPH EASNARGILE   300
LYSASNASNV ALALALEUGL YGLUALALEU EULEU ASNLYSILEI LEASNALAIL EPROTYRLEU   360
GLYASNSERT YRSERLEULE UASPLYSPHE ASPTHRASNS ERASNSERVA LSERPHEASN   420
LEULEUGLUG LNASPPROSE RGLYALATHR THRLYSSERA LAMETLEUTH RASNLEUILE   480
ILEPHEGLYP ROGLYPROVA LLEUASNLYS ASNGLUVALA RGGLYILEVA LEUARGVAL   540
ASPASNLYSA SNTYRPHEPR OCYSARGASP GLYPHEGLYS ERILEMETGL NMETALAPHE   600
CYSPROGLUT YRVALPROTH RPHEASPASN VALILEGLUA SNILETHRSE RLEUTHRILE   660
GLYLYSSERL YSTYRPHEGL NASPPROALA LEULEULEUM ETHISALALE UILEHISVAL   720
LEUHISGLYL EUTYRGLYME TGLNVALSER SERHISGLUI LEILEPROSE RLYSGLNLEU   780
ILETYRMETG LNHISTHRTY RPROILESER ALAGLULALL EUPHETHRPH EGLYGLYGLN   840
ASPALAASNL EUILESERIL EASPILELYS ASNASPLEUT YRGLULYSTH RLEUASNASP   900
TYRLYSALAI LEALAASNLY SLEUSERGLN VALTHRSERC YSASNASPPR OASNILEASP   960
ILEASPSERT YRLYSGLNIL ETYRGLNGLN LYSTYRGLNP HEASPLYSAS PSERASNGLY  1020
GLNTYRILEV ALASNGLUAS PLYSPHEGLN ILELEUTYRA SNSERILEME TTYRGLYPHE  1080
THRGLUILEG LULEUGLYLY SLYSPHEASN ILELYSTHRA RGLEUSERTY RPHESERMET  1140
ASNHISASPP ROVALLYSIL EPROASNLEU LEUASPASPT HRILETYRAS NASPTHRGLU  1200
GLYPHEASNI LEGLUSERLY SASPLEULYS SERGLUTYRL YSGLYGLNAS NMETARGVAL  1260
ASNTHRASNA LAPHEARGAS NVALASPGLY SERGLYLEUV ALSERLYSLE UILEGLYLEU  1320
CYSLYSLYSI LEILEPROPR OTHRASNILE ARGGLUASNL EUTYRASNAR GTHRALASER  1380
LEUTHRASPL EUGLYGLYGL ULEUCYSILE LYSILELYSA SNGLUASPLE UTHRPHEILE  1440
ALAGLULYSA SNSERPHESE RGLUGLUPRO PHEGLNASPG LUILEVALSE RTYRASNTHR  1500
LYSASNLYSP ROLEUASNPH EASNTYRSER LEUASPLYSI LEILELEUAS PTYRASNLEU  1560
GLNSERLYSI LETHRLEUPR OASNASPARG THRTHRPROV ALTHRLYSGL YILEPROTYR  1620
ALAPROGLUT YRLYSSERAS NALAALASER THRILEGLUI LEHISASNIL EASPASPASN  1680
THRILETYRG LNTYRLEUTY RALAGLNLYS SERPROTHRT HRLEUGLNAR GILETHRMET  1740
THRASNSERV ALASPASPAL ALEUILEASN SERTHRLYSI LETYRSERTY RPHEPROSER  1800
VALILESERL YSVALALASN GLNGLYALAG LN GLYILELELEUP HELEUGLNTR PVALARGASP  1860
ILEILEASPA SPPHETHRAS NGLUSERSER GLNLYSTHRT HRILEASPLY SILESERASP  1920
VALSERTHRI LEVALPROTY RILEGLYPRO ALALEUASNI LEVALLYSGL NGLYTYRGLU  1980
GLYASNPHEI LEGLYLYALALE UGLUTHRTHR GLYVALVALL EULEULEUGL UTYRILEPRO  2040
GLUILETHRL EUPROVALIL EALAALALEU SERILEALAG LUSERSERTH RGLNLYSGLN  2100
LYSILEILEL YSTHRILEAS PASNPHELEU GLULYSARGT YRGLULYSTR PILEGLUVAL  2160
TYRLYSLEUV ALLYSALALY STRPLEUGLY THRVALASNT HRGLNPHEGL NLYSARGSER  2220
TYRGLNMETT YRARGSERLE UGLUTYRGLN VALASPALAI LELYSLYSIL EILEASPTYR  2280
GLUTYRLYSI LETYRSERGL YPROASPLYS GLUGLNILEA LAASPGLUIL EASNASNLEU  2340
LYSASNLYSL EUGLUGLULY SALAASNLYS ALAMETILEA SNILEASNIL EPHEMETARG  2400
GLUSERSERA RGSERPHELE UVALASNGLN METILEASNG LUALALYSLY SGLNLEULEU  2460
```

```
GLUPHEASPT HRGLNSERLY SASNILELEU METGLNTYRI LELYSALAAS NSERLYSPHE   2520
ILEGLYILET HRGLULEULY SLYSLEUGLU SERLYSILEA SNLYSVALPH ESERTHRPRO   2580
ILEPROPHES ERTYRSERLY SASNLEUASP CYSTRPVALA SPASNGLUGL UASPILEASP   2640
VALILELEUL YSLYSSERTH RILELEUASN LEUASPILEA SNASNASPIL EILESERASP   2700
ILESERGLYP HEASNSERSE RVALILETHR TYRPROASPA LAGLNLEUVA LPROGLYILE   2760
ASNGLYLYSA LAILEHISLE UVALASNASN GLUSERSERG LUVALILEVA LHISLYSALA   2820
METASPILEG LUTYRASNAS PMETPHEASN ASNPHETHRV ALSERPHETR PLEUARGVAL   2880
PROLYSVALS ERALASERHI SLEUGLUGLN TYRGLYTHRA SNGLUTYRSE RILEILESER   2940
SERMETLYSL YSTYRSERLE USERILEGLY SERGLYTRPS ERVALSERLE ULYSGLYASN   3000
ASNLEUILET RPTHRLEULY SASPSERALA GLYGLUVALA RGGLNILETH RPHEARGASP   3060
LEUSERASPL YSPHEASNAL ATYRLEUALA ASNLYSTRPV ALPHEILETH RILETHRASN   3120
ASPARGLEUS ERSERALAAS NLEUTYRILE ASNGLYVALL EUMETGLYSE RALAGLUILE   3180
THRGLYLEUG LYALAILEAR GGLUASPASN ASNILETHYL EULYSLEUAS PARGCYSASN   3240
ASNASNASNG LNTYRVALSE RILEASPLYS PHEARGILEP HECYSLYSAL ALEUASNPRO   3300
LYSGLUILEG LULYSLEUTY RTHRSERTYR LEUSERILET HRPHELEUAR GASPPHETRP   3360
GLYASNPROL EUARGTYRAS PTHRGLUTYR TYRLEUILEP ROVALALASE RSERSERLYS   3420
ASPVALGLNL EULYSASNIL ETHRASPTYR METTYRLEUT HRASNALAPR OSERTYRTHR   3480
ASNGLYLYSL EUASNILETY RTYRARGARG LEUTYRASNG LYLEULYSPH EILEILELYS   3540
ARGTYRTHRP ROASNASNGL UILEASPSER PHEVALLYSS ERXAAASPPH EILEILELYS   3600
TYRVALSERT YRASNASNAS NGLUHISILE VALGLYTYRP ROLYSASPGL YASNALAPHE   3660
ASNASNLEUA SPARGILELE UARGVALGLY TYRASNALAP ROGLYILEPR OLEUTYRLYS   3720
LYSMETGLUA LAVALLYSLE UARGASPLEU LYSTHRTYRS ERVALGLNLE ULYSLEUTYR   3780
ASPASPLYSA SNALASERLE UGLYLEUVAL GLYTHRHISA SNGLYGLNIL EGLYASNASP   3840
PROASNARGA SPILELEUIL EALASERASN TRPTYRPHEA SNHISLEULY SASPLYSILE   3900
LEUGLYCYSA SPTRPTYRPH EVALPROTHR ASPGLUGLYT RPTHRASNAS PHISHISHIS   3960
HISHISHISG LYLEUGLNPR OSERLEUILE SERALATRPT HRPROVALAS PARGSERSER   4020
ASNASPLEUA RGTHRPROSE RGLYPHEVAL GLNASNALAA RGLEUPROPR OGLYVALPHE   4080
TYRTRPGLUS ERLYSLEUAL ATRPARGASP PHEGLNGLUL EUARGLYSLE U            4131
```

```
SEQ ID NO: 3               moltype = DNA   length = 3948
FEATURE                    Location/Qualifiers
source                     1..3948
                           mol_type = genomic DNA
                           organism = Clostridium tetani
SEQUENCE: 3
atgccaataa ccataaataa ttttagatat agtgatcctg ttaataatga tacaattatt     60
atgatggagc caccatactg taagggtcta gatatctatt ataaggcttt caaaataaca    120
gatcgtattt ggatagtgcc ggaaaggtat gaatttggga caaaacctga agattttaac    180
ccaccatctt cattaataga aggtgcatct gagtattacg atccaaatta tttaaggact    240
gattctgata aagatagatt tttacaaacc atggtaaaac tgtttaacag aattaaaaac    300
aatgtagcag gtgaagcctt attagataag ataataaatg ccatacctta ccttggaaat    360
tcatattcct tactagacaa gtttgataca aactctaatt cagtatcttt taatttatta    420
gaacaagacc ccagtggagc aactacaaaa tcagcaatgc tacaaatttt aataattatt    480
ggacctgggc ctgttttaaa taaaaatgag gttagaggta ttgtattgag ggtagataat    540
aaaaattact tcccatgtag agatggtttt ggctcaataa tgcaaatggc attttgccca    600
gaatatgtac ctacctttga taatgtaata gaaaatatta cgtcactcac tattggcaaa    660
agcaaatatt ttcaagatcc agcattacta ttaatgcacg aacttataca tgtactacat    720
ggtttatacg gaatgcaggt atcaagccat gaaattattc catccaaaca agaaatttat    780
atgcagcata catatccaat aagtgctgaa gaactattca cttttggcgg acaggatgct    840
aatcttataa gtattgatat aaaaaacgat ttatatgaaa aactttaaa tgattataaa    900
gctatagcta caaacttag tcaagtcact agctgcaatg atcccaacat tgatattgat    960
agctacaaac aaatatatca acaaaaatat caattcgata agatagcaa tggacaatat   1020
attgtaaatg aggataaatt tcagatacta taatagca taatgtatgg ttttacagag   1080
attgaattgg gaaaaaaatt taatataaaa actagacttt tcttattttag tatgaatcat   1140
gaccctgtaa aaattccaaa tttattagat gatcaatttt acaatgatac agaaggattt   1200
aatatagaaa gcaagatctc gaaatctgaa tataaaggac aaaatgagg ggtaaataca   1260
aatgctttta gaaatgttga tggatcaggc ctagtttcaa aacttattgg cttatgtaaa   1320
aaaattatac cacaacaaa tataagagaa aatttatata tagaactgc atcattaaca   1380
gatttaggag gagaattatg tataaaaatt aaaaatgaag atttaacttt tatagctgaa   1440
aaaaatagct tttcagaaga accatttcaa gatgaaatag ttagttataa tacaaaaaat   1500
aaaccattaa atttaatta ttcgctagat aaaattattg tagattataa tctacaaagt   1560
aaaattacat tacctaatga taggacaacc ccagttacaa aggaattcc atatgctcca   1620
gaatataaaa gtaatgctgc aagtacaata gaaatacata atattgatga caatacaata   1680
tatcaatatt tgtatgctca aaaatctcct acaactctac aaagaataac tatgactaat   1740
tctgttgatg acgcattaat aaattccacc aaaatatatt catatttcc atctgtaatc   1800
agtaaagtta accaaggtgc acaaggaatt ttattcttac agtgggtgag agatataatt   1860
gatgatttta ccaatgaatc ttcacaaaaa actactattg ataaaatttc agatgtatcc   1920
actattgttc cttatatagg acccgcatta aacattgtaa aacaaggcta tgagggaaac   1980
tttataggcg ctttgaaaac taccggagtg gttttattat tagaatatat tccagaaatt   2040
actttaccag taattgcagc tttatctata gcagaaagta gcacacaaaa agaaaagata   2100
ataaaaacaa tagataactt tttagaaaaa agatatgaaa atggattga gtatataaaa   2160
ctagtaaaag caaaatggtt aggcacagtt aatacgcaat ccaaaaaag aagttatcaa   2220
atgtatagat ctttagaata tcaagtagat gcaataaaaa aataatgaga ctatgaatat   2280
aaatatatt caggacctga taaggaacaa atgccgacg aaattaataa tctgaaaaac   2340
aaacttgaag aaaaggctaa taagcaatg ataaacataa atatattat gaggqaaagt   2400
tctagatcat tttagttaa tcaaatgatt aacgaagcta aaaagcagtt attagagttt   2460
gatactcaaa gcaaaatat tttaatgcag tatataaaag caattctaa atttataggt   2520
ataactgaac taaaaaaatt agaatcaaaa ataaacaaag ttttttcaac accaattcca   2580
ttttcttatt ctaaaaatct ggattgttgg gttgataatg aagaagatat agatgttata   2640
```

-continued

```
ttaaaaaaga gtacaatttt aaatttagat attaataatg atattatatc agatatatct 2700
gggtttaatt catctgtaat aacatatcca gatgctcaat tggtgcccgg aataaatggc 2760
aaagcaatac atttagtaaa caatgaatct tctgaagtta tagtgcataa agctatggat 2820
attgaatata atgatatgtt taataatttt accgttagct tttggttgag ggttcctaaa 2880
gtatctgcta gtcatttaga acaatatggc acaaatgagt attcaataat tagctctatg 2940
aaaaaacata gtctatcaat aggatctggt tggagtgtat cacttaaagg taataactta 3000
atatggactt taaagattc cgcgggagaa gttagacaaa taacttttag ggatttacct 3060
gataaattta atgcttattt agcaaataaa tgggttttta taactattac taatgataga 3120
ttatcttctg ctaatttgta tataaatgga gtacttatgg gaagtgcaga aattactggt 3180
ttaggagcta ttagagagga taataatata acattaaaac tagatagatg taataataat 3240
aatcaatacg tttctattga taaatttagg atattttgca aagcattaaa tccaaaagag 3300
attgaaaaat tatacacaag ttatttatct ataacctttt taagagactt ctggggaaac 3360
cctttacgat atgatacaga atattattta ataccagtag cttctagttc taaagatgtt 3420
caattgaaaa ataaacaga ttatatgtat ttgacaaatg cgccatcgta tactaacgga 3480
aaattgaata tatattatag aaggttatat aatggactaa aatttattat aaaaagatat 3540
acacctaata atgaaataga ttctttttgtt aaatcaggtg attttattaa attatatgta 3600
tcatataaca ataatgagca cattgtaggt tatccgaaag atggaaatgc ctttaataat 3660
cttgatagaa ttctaagagt aggttataat gccccaggta tccctcttta taaaaaaatg 3720
gaagcagtaa aattgcgtga tttaaaaacc tattctgtac aacttaaatt atatgatgat 3780
aaaaatgcat ctttaggact agtaggtacc cataatggtc aaataggcaa cgatccaaat 3840
agggatatat taattgcaag caactggtac tttaatcatt taaaagataa aattttagga 3900
tgtgattggt actttgtacc tacagatgaa ggatggacaa atgattaa         3948
```